United States Patent
Liu et al.

(10) Patent No.: US 8,222,280 B2
(45) Date of Patent: Jul. 17, 2012

(54) ETHER COMPOUNDS WITH NITROGEN-CONTAINING 5-MEMBER HETEROCYCLE AND USES THEREOF

(75) Inventors: Changling Liu, Shenyang (CN); Miao Li, Shenyang (CN); Junfeng Wang, Shenyang (CN); Jinbo Zhang, Shenyang (CN); Hong Zhang, Shenyang (CN); Shulin Hao, Shenyang (CN); Jing Zhang, Shenyang (CN); Jichun Yang, Shenyang (CN)

(73) Assignees: Sinochem Corporation, Beijing (CN); Shenyang Research Institute of Chemical Industry Co., Ltd., Shenyang (CN)

( * ) Notice: Subject to any disclaimer, the term of this patent is extended or adjusted under 35 U.S.C. 154(b) by 0 days.

(21) Appl. No.: 13/121,334

(22) PCT Filed: Nov. 25, 2009

(86) PCT No.: PCT/CN2009/075131
§ 371 (c)(1),
(2), (4) Date: Mar. 28, 2011

(87) PCT Pub. No.: WO2010/060379
PCT Pub. Date: Jun. 3, 2010

(65) Prior Publication Data
US 2011/0178149 A1 Jul. 21, 2011

(30) Foreign Application Priority Data
Nov. 28, 2008 (CN) .......................... 2008 1 0227711

(51) Int. Cl.
*A61K 31/44* (2006.01)
*A61K 31/427* (2006.01)
*A61K 31/415* (2006.01)
*C07D 401/02* (2006.01)
*C07D 277/20* (2006.01)
*C07D 231/10* (2006.01)

(52) U.S. Cl. ..... 514/341; 514/365; 514/406; 546/275.4; 548/203; 548/373.1

(58) Field of Classification Search ............... 548/370.4, 548/203, 373.1; 514/341, 365, 406; 546/275.4
See application file for complete search history.

(56) References Cited

U.S. PATENT DOCUMENTS
6,949,551 B2 * 9/2005 Tiebes et al. ............... 514/252.1

2004/0029886 A1 2/2004 Tiebes et al.
2009/0192208 A1 7/2009 Takyo et al.
2011/0178149 A1 7/2011 Liu

FOREIGN PATENT DOCUMENTS

| CN | 1761654 A | 4/2006 |
|---|---|---|
| CN | 1914178 A | 2/2007 |
| EP | 0787710 A1 | 8/1997 |
| WO | 96/11909 A1 | 4/1996 |
| WO | 9611909 A1 | 4/1996 |
| WO | 2005019147 A2 | 3/2005 |
| WO | 2010/060379 A1 | 6/2010 |

OTHER PUBLICATIONS

International Search Report received in PCT/CN2009/075131 mailed Mar. 11, 2010.

* cited by examiner

*Primary Examiner* — Rebecca Anderson
*Assistant Examiner* — Samantha Shterengarts
(74) *Attorney, Agent, or Firm* — Smith, Gambrell & Russell, LLP

(57) ABSTRACT

The invention relates to ether compounds with nitrogen-containing 5-member heterocycle, represented by formula (I):

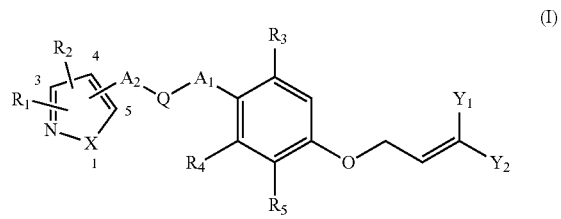

The groups are as defined as specification.

The compounds of the present invention have broad-spectrum insecticidal activities, and they are very effective to lepidopterous pests, including *Ostrinia nubilalis*, sugarcane borer, summer fruit tortrix moth, *Grapholitha inopinata*, *Lymantria dispar*, *Cnaphalocrocis medialis*, *Pyrausta nubilalis*, *Heliothis assulta*, *Grapholitha molesta*, *Plutella xylostella*, *Laphygma exigua*, *Prodenialitura* and the like, especially more effective to *Plutella xylostella* and *Laphygma exigua*, and can have very good effects at very low doses. And the compounds of present invention have high activities to homopteran pests such as aphid. At the same time, some compounds of present invention have very good fungicidal activities, and can be used for preventing wheat powdery mildew, cucumber downy mildew, vegetable grey mould and the like.

8 Claims, No Drawings

ETHER COMPOUNDS WITH NITROGEN-CONTAINING 5-MEMBER HETEROCYCLE AND USES THEREOF

FIELD OF THE INVENTION

The present invention relates to insecticide, fungicide. Specifically to ether compounds with nitrogen-containing 5-member heterocycle and the uses as insecticide or fungicide in agriculture or other fields thereof.

BACKGROUND OF THE INVENTION

It is well known that insects in general can cause significant damage, not only to crop growth in agriculture, but also, for example, to constructions and turf where the damage is caused by soil-borne insects (such as termites and white grubs).

Such damage may result in the loss of millions of dollars concerning crop, turf or constructions. Insecticides and acaricides are useful for controlling insects and acarids, but may cause significant damage to crops such as wheat, corn, soybeans, potatoes and cotton. For crop protection, insecticides and acaricides are desired which can control the insects and acarids while without damaging the crops, and have no deleterious effects to mammals and other living organisms.

The following patents disclosed a variety of dihalopropene compounds with insecticidal and acaricidal activities: CN1137265, CN1318535, CN1681771, CN1780818, CN1780825, CN1860874, CN101208088, U.S. Pat. No. 5,872,137, U.S. Pat. No. 5,922,880, U.S. Pat. No. 6,071,861, US20060247283, US20050288186, US20040224994, US20070142229 and WO2003074498 etc. However, there is no report whether the dihalopropene compounds have fungicidal activity. Meanwhile people will still need to continue developing novel insecticide and fungicide in order to prevent diseases and insect pests in agricultural or other fields. The representative compound Pyridalyl is a patent product of Japan sumitomo chemical Co., Ltd, and has good insecticidal activity against *lepidoptera* of vegetables and cotton. The structure is as follows:

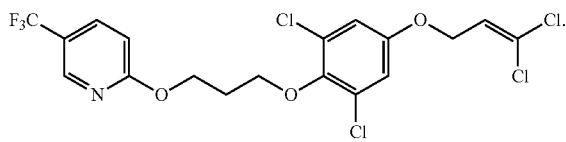

SUMMARY OF THE INVENTION

The object of the present invention is to provide ether compounds with nitrogen-containing 5-member heterocycle with biological activity against all sorts of crops diseases and insects at very low doses, the another of the present invention is to provide compounds which can be applied in agriculture to control diseases and insects in plant or used as insecticides and fungicides in other fields.

Detailed description of the invention is as follows:

The present invention provides ether compounds with nitrogen-containing 5-member heterocycle having general formula I:

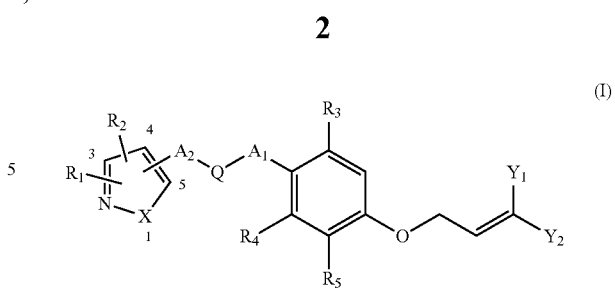

wherein:

$R_1$ is selected from H, $CO_2R_6$, $C_1$-$C_{12}$alkyl, $C_1$-$C_{12}$haloalkyl, $C_1$-$C_{12}$alkoxy$C_1$-$C_{12}$alkyl, $C_1$-$C_{12}$haloalkoxy$C_1$-$C_{12}$alkyl, $C_3$-$C_6$cycloalkyl or $R_7$;

$R_2$ is selected from H, halo, CN, $CO_2R_6$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_3$-$C_6$cycloalkyl or $R_7$;

$R_3$, $R_4$ and $R_5$ mutually independently may be the same or different, selected from H, halo, OH, SH, CN, $NO_2$, $C_1$-$C_{12}$alkyl, $C_1$-$C_{12}$haloalkyl, $C_1$-$C_{12}$alkylcarbonyl, $C_2$-$C_{12}$alkenyl, $C_2$-$C_{12}$haloalkenyl, $C_2$-$C_{12}$alkynyl, $C_1$-$C_{12}$alkoxy, $C_1$-$C_{12}$haloalkoxy, $C_2$-$C_{12}$alkenyloxy, $C_2$-$C_{12}$haloalkenyloxy, $C_3$-$C_{12}$alkynyloxy, $C_3$-$C_{12}$haloalkynyloxy, $C_1$-$C_{12}$alkylthio, $C_1$-$C_{12}$haloalkylthio, $C_1$-$C_{12}$alkylsulfonyl, $C_1$-$C_{12}$alkylsulfinyl, $C_1$-$C_{12}$alkoxy$C_1$-$C_{12}$alkyl, $C_1$-$C_{12}$alkoxycarbonyl, $C_1$-$C_{12}$alkoxycarbonyl$C_1$-$C_{12}$alkyl, or $C_1$-$C_{12}$haloalkoxy$C_1$-$C_{12}$alkyl;

X is selected from $NR_8$ or O;

$R_8$ is selected from H, $C_1$-$C_{12}$alkyl, $C_1$-$C_{12}$haloalkyl, $C_1$-$C_{12}$alkoxy$C_1$-$C_{12}$alkyl, $C_1$-$C_{12}$haloalkoxy$C_1$-$C_{12}$alkyl, $C_3$-$C_6$cycloalkyl or $R_7$;

$Y_1$ and $Y_2$ mutually independently may be the same or different, selected from H, F, Cl, Br, $CH_3$, CN or $CF_3$;

$A_1$ and $A_2$ mutually independently may be the same or different, selected from O, S or $NR_6$;

$R_6$ is selected from H or $C_1$-$C_{12}$alkyl;

$R_7$ is selected from aryl, heteroaryl, aryl$C_1$-$C_{12}$alkyl or heteroaryl$C_1$-$C_{12}$alkyl, or above group substituted with 1-5 substitutents selected from halo, $NO_2$, CN, $CO_2R_6$, $CONHR_6$, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfonyl or $R_7$;

Q is selected from —$CH_2$—, —$CH_2CH_2$—, —$CH_2CH_2CH_2$—, —$CH_2CH_2CH_2CH_2$—, —$CH_2CH_2CH_2CH_2CH_2$—, —$CH(CH_3)$—, —$CH(CH_3)CH_2$—, —$CH(CH_3)CH_2CH_2$—, —$CH_2CH_2CH(CH_3)$—, —$CH(C_2H_5)$—, —$C(CH_3)_2$—, —$CH(CH_3)CH(CH_3)$—, —$CH_2C(CH_3)_2CH_2$—, —$CH_2CH_2OCH_2CH_2$—, —$CH_2CH_2NHCH_2CH_2$—, —$CH_2CH_2SCH_2CH_2$—, —$CH_2CH_2SO_2CH_2CH_2$—, —$CH_2COCH_2$—, —$COCH_2CO$—, —$CH_2CH_2CO$—, —$COCH_2CH_2$—, —$CH_2CO$—, —$COCH_2$—, —$CH_2C(=NOCH_3)CH_2$—, —$CH_2C(=NN(CH_3)_2)CH_2$—, —$CH_2CH(OH)CH_2$—, —$CH_2CH(OCH_3)CH_2$—, —$CH_2CH(OCOCH_3)CH_2$— or

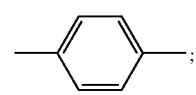

;

$A_2$ links with heterocycle at the 3, 4 or 5-position; when $A_2$ links with heterocycle at the 5-position, $R_1$ is at 3-position, $R_2$ is at 4-position; when $A_2$ links with heterocycle at the 3-position, R₁ is at 5-position, R₂ is at 4-position; when A₂ links with heterocycle at the 4-position, R₁ is at 3-position, R₂ is at 5-position.

The preferred compounds of general formula (I) of this invention are:

R₁ is selected from H, CO₂R₆, C₁-C₆alkyl, C₁-C₆haloalkyl, C₁-C₆alkoxyC₁-C₆alkyl, C₁-C₆haloalkoxyC₁-C₆alkyl, C₃-C₆cycloalkyl or R₇;

R₂ is selected from H, halo, CN, CO₂R₆, C₁-C₆alkyl, C₁-C₆haloalkyl, C₁-C₆alkoxy, C₁-C₆haloalkoxy, C₁-C₆alkylthio, C₁-C₆haloalkylthio, C₃-C₆cycloalkyl or R₇;

R₃, R₄ and R₅ mutually independently may be the same or different, selected from H, halo, or C₁-C₆alkyl;

X is selected from NR₈ or O;

R₈ is selected from H, C₁-C₆alkyl, C₁-C₆haloalkyl, C₁-C₆alkoxyC₁-C₆alkyl, C₁-C₆haloalkoxyC₁-C₆alkyl, C₃-C₆cycloalkyl or R₇;

Y₁ and Y₂ mutually independently may be the same or different, selected from H, F, Cl, Br, CH₃, CN or CF₃;

A₁ and A₂ mutually independently may be the same or different, selected from O, S or NR₆;

R₆ is selected from H or C₁-C₆alkyl;

R₇ is selected from phenyl, pyridinyl, pyrimidinyl, triazolyl, oxazolyl, thiadiazolyl, oxadiazolyl, furanyl, thiophen, thiazolyl, benzyl, pyridylmethyl, thiophenylmethyl or thiazolylmethyl, or above group substituted with 1-3 substitutents selected from halo, NO₂, CN, CO₂R₆, CONHR₆, C₁-C₆alkyl, C₁-C₆haloalkyl, C₁-C₆alkoxy, C₁-C₆haloalkoxy, C₁-C₆alkylthio, C₁-C₆alkylsulfonyl, phenyl, 4-chloro-phenyl, phenoxy or 4-chloro-phenoxy;

Q is selected from —CH₂CH₂—, —CH₂CH₂CH₂—, —CH₂CH₂CH₂CH₂—, —CH₂COCH₂— or

A₂ links with heterocycle at the 3, 4 or 5-position; when A₂ links with heterocycle at the 5-position, R₁ is at 3-position, R₂ is at 4-position; when A₂ links with heterocycle at the 3-position, R₁ is at 5-position, R₂ is at 4-position; when A₂ links with heterocycle at the 4-position, R₁ is at 3-position, R₂ is at 5-position.

Further more, the preferred compounds of general formula (I) of this invention are:

R₁ is selected from H, CO₂R₆, C₁-C₆alkyl, C₁-C₆haloalkyl, C₁-C₆alkoxyC₁-C₆alkyl, C₁-C₆haloalkoxyC₁-C₆alkyl, C₃-C₆cycloalkyl or R₇;

R₂ is selected from H, halo, CN, CO₂R₆, C₁-C₆alkyl, C₁-C₆haloalkyl, C₁-C₆alkoxy, C₁-C₆haloalkoxy, C₁-C₆alkylthio, C₁-C₆haloalkylthio, C₃-C₆cycloalkyl or R₇;

R₃ is Cl;

R₄ and R₅ mutually independently may be the same or different, selected from H or Cl;

X is selected from NR₈ or O;

R₈ is selected from C₁-C₆alkyl, C₁-C₆haloalkyl or R₇;

Y₁ and Y₂ are Cl;

A₁ and A₂ are O;

R₆ is selected from H or C₁-C₆alkyl;

R₇ is selected from phenyl, pyridinyl, furanyl, thiophen, thiazolyl or benzyl, or above group substituted with 1-3 substitutents selected from halo, NO₂, CN, CO₂R₆, CONHR₆, C₁-C₆alkyl, C₁-C₆haloalkyl, C₁-C₆alkoxy, C₁-C₆haloalkoxy, C₁-C₆alkylthio, C₁-C₆alkylsulfonyl, phenyl, 4-chloro-phenyl, phenoxy or 4-chloro-phenoxy;

Q is selected from —CH₂CH₂—, —CH₂CH₂CH₂— or —CH₂CH₂CH₂CH₂—;

A₂ links with heterocycle at the 3, 4 or 5-position; when A₂ links with heterocycle at the 5-position, R₁ is at 3-position, R₂ is at 4-position, the structure is represented by general formula I-1; when A₂ links with heterocycle at the 3-position, R₁ is at 5-position, R₂ is at 4-position, the structure is represented by general formula I-2; when A₂ links with heterocycle at the 4-position, R₁ is at 3-position, R₂ is at 5-position, the structure is represented by general formula I-3;

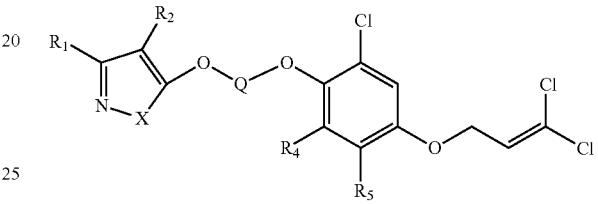

I-1

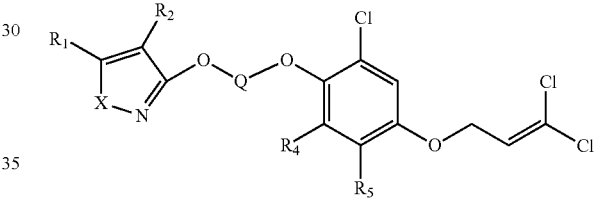

I-2

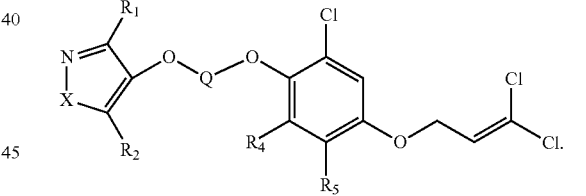

I-3

Even more preferred compounds of formula (I-1) or formula (I-2) of this invention are:

R₁ is selected from H, CO₂R₆, C₁-C₆alkyl, C₁-C₆haloalkyl, C₁-C₆alkoxyC₁-C₆alkyl, C₁-C₆haloalkoxyC₁-C₆alkyl, C₃-C₆cycloalkyl or R₇;

R₂ is selected from H, F, Cl, Br, CN, CO₂R₆ or C₁-C₆alkyl;

R₄ and R₅ mutually independently may be the same or different, selected from H or Cl;

X is NR₈;

R₈ is C₁-C₄alkyl;

R₆ is selected from H or C₁-C₄alkyl;

R₇ is selected from phenyl, or phenyl substituted with 1-3 substituents selected from F, Cl, Br, C₁-C₆alkyl, C₁-C₆haloalkyl, C₁-C₆alkoxy, C₁-C₆haloalkoxy or C₁-C₆alkylthio;

Q is selected from —CH₂CH₂—, —CH₂CH₂CH₂— or —CH₂CH₂CH₂CH₂—; Or, the compounds of formula (I-3) are:

$R_1$ is selected from H, $CO_2R_6$ or $C_1$-$C_6$alkyl;

$R_2$ is selected from H, F, Cl, Br or $C_1$-$C_6$alkyl;

$R_4$ and $R_5$ mutually independently may be the same or different, selected from H or Cl;

X is $NR_8$;

$R_8$ is selected from $C_1$-$C_4$alkyl or $R_7$;

$R_6$ is selected from H or $C_1$-$C_4$alkyl;

$R_7$ is selected from phenyl, or phenyl substituted with 1-3 substitutents selected from F, Cl, Br, CN, $C_1$-$C_6$alkyl, $C_1$-$C_6$haloalkyl, $C_1$-$C_6$alkoxy, $C_1$-$C_6$haloalkoxy or $C_1$-$C_6$alkylthio;

Q is selected from —$CH_2CH_2$—, —$CH_2CH_2CH_2$— or —$CH_2CH_2CH_2CH_2$—.

Most preferred compounds of formula (I-1) or formula (I-2) of this invention are:

$R_1$ is selected from phenyl, or phenyl substituted with 1-3 substituents selected from F, Cl, Br, $C_1$-$C_4$alkyl, $C_1$-$C_4$haloalkyl, $C_1$-$C_4$alkoxy, $C_1$-$C_4$haloalkoxy or $C_1$-$C_4$alkylthio;

$R_2$ is selected from H, $C_1$ or $C_1$-$C_4$alkyl;

$R_4$ and $R_5$ mutually independently may be the same or different, selected from H or Cl;

X is $NR_8$;

$R_8$ is $C_1$-$C_4$alkyl;

$R_6$ is selected from H or $C_1$-$C_4$alkyl;

Q is selected from —$CH_2CH_2$—, —$CH_2CH_2CH_2$— or —$CH_2CH_2CH_2CH_2$—; Or, the compounds of formula (I-3) are:

$R_1$ is selected from H, $CO_2R_6$ or $C_1$-$C_4$alkyl;

$R_2$ is selected from H, F, Cl, Br or $C_1$-$C_4$alkyl;

$R_4$ and $R_5$ mutually independently may be the same or different, selected from H or Cl;

X is $NR_8$;

$R_8$ is selected from $C_1$-$C_4$alkyl, phenyl, or phenyl substituted with 1-3 substituents selected from F, Cl, Br, $C_1$-$C_4$alkyl, $C_1$-$C_4$haloalkyl, $C_1$-$C_4$alkoxy or $C_1$-$C_4$haloalkoxy;

$R_6$ is selected from H or $C_1$-$C_4$alkyl;

Q is selected from —$CH_2CH_2$—, —$CH_2CH_2CH_2$— or —$CH_2CH_2CH_2CH_2$—.

It must be noted that, as used in this specification, the appended claims and the general formula (I), The "unsubstituent(s)" denote(s) all the substitute group(s) is (are) H.

The "halo" denotes fluorine, chlorine, bromine or iodine.

The "alkyl" stands for straight-chain or branched alkyl, such as methyl, ethyl, propyl, isopropyl or tert-butyl.

The "haloalkyl" stands for straight or branched chain alkyl, in which hydrogen atom can be all or partly substituted with halogen, such as chloromethyl, dichloromethyl, trichloromethyl, fluoromethyl, difluoromethyl, trifluoromethyl.

The "alkenyl" stands for a straight-chain or branched, having double bonds at any position such as vinyl or allyl.

The "alkynyl" stands for a straight-chain or branched, having triple bonds at any position such as ethynyl, propynyl.

The aryl and aryl in arylalkyl include phenyl or naphthyl etc.

The "heteroaryl" in this invention stands for five member ring or six member ring containing one or more N, O, S hetero atoms. Such as pyridinyl, furanyl, pyrimidinyl, pyrazinyl, pyridazinyl, triazinyl, quinolinyl, thiazolyl, benzothiazolyl or benzofuranyl.

The preferred groups and substituents of $R_1$ and $R_2$ in preferred general formula (I-1), (I-2), (I-3) of this invention refer to Tables 1-9.

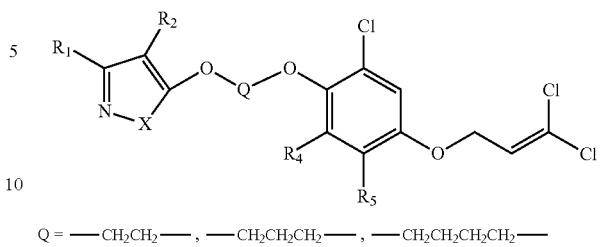

I-1

Q = —$CH_2CH_2$—, —$CH_2CH_2CH_2$—, —$CH_2CH_2CH_2CH_2$—

$R_4$ and $R_5$ mutually independently may be the same or different, selected from H or Cl.

In the general formula (I-1): When $R_1$ is phenyl, the substituted groups of phenyl refer to Table 1. When $R_1$ is pyridinyl, the substituted groups of pyridinyl refer to Tables 2-4. When $R_1$ is thiazolyl, the substituted groups of thiazolyl refer to Table 5. When $R_1$ is thiophene or furanyl, the substituted groups of furan refer to Tables 6-7. When $R_1$ is other groups, the substituted groups refer to Table 8.

In the general formula (I-1): When $R_2$ is phenyl, the substituted groups of phenyl refer to Table 1. When $R_2$ is pyridinyl, the substituted groups of pyridinyl refer to Tables 2-4. When $R_2$ is thiazolyl, the substituted groups of thiazolyl refer to Table 5. When $R_2$ is thiophene or furanyl, the substituted groups of furan refer to Tables 6-7. When $R_2$ is other groups, the substituted groups refer to Table 9.

$R_1$, $R_2$ in general formula (I-2), (I-3) are defined as that in general formula (I-1).

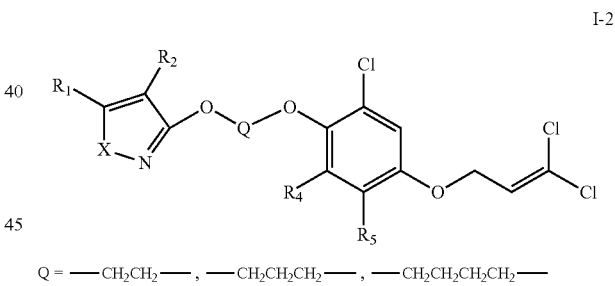

I-2

Q = —$CH_2CH_2$—, —$CH_2CH_2CH_2$—, —$CH_2CH_2CH_2CH_2$—

—$R_4$ and $R_5$ mutually independently may be the same or different, selected from H or Cl.

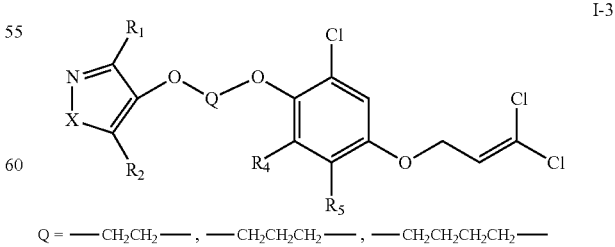

I-3

Q = —$CH_2CH_2$—, —$CH_2CH_2CH_2$—, —$CH_2CH_2CH_2CH_2$—

$R_4$ and $R_5$ mutually independently may be the same or different, selected from H or Cl.

TABLE 1

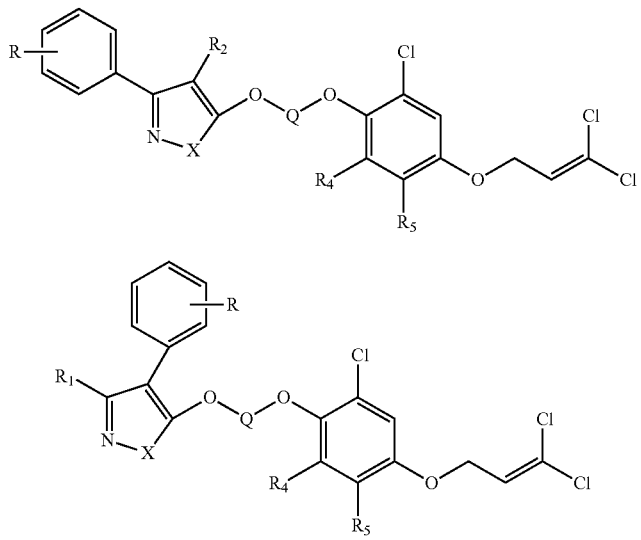

| R | R | R | R | R | R | R |
|---|---|---|---|---|---|---|
| H | 2-NO$_2$ | 2-SO$_2$C$_2$H$_5$ | 2,3-2F | 2,3-2CH$_3$ | 2-Cl-4-F | 4-CH$_3$-2-Br |
| 2-F | 3-NO$_2$ | 3-SO$_2$C$_2$H$_5$ | 2,4-2F | 2,4-2CH$_3$ | 2-Cl-4-Br | 4-CH$_3$-2-Cl |
| 3-F | 4-NO$_2$ | 4-SO$_2$C$_2$H$_5$ | 2,5-2F | 2,5-2CH$_3$ | 2-Cl-4-I | 2,4,6-3CH$_3$ |
| 4-F | 2-SCF$_3$ | 2-CO$_2$CH$_3$ | 2,6-2F | 2,6-2CH$_3$ | 3-Cl-4-I | 2,4,6-3C$_2$H$_5$ |
| 2-Cl | 3-SCF$_3$ | 3-CO$_2$CH$_3$ | 3,4-2F | 3,4-2CH$_3$ | 4-Cl-2-Br | 2-NHCOCH$_3$ |
| 3-Cl | 4-SCF$_3$ | 4-CO$_2$CH$_3$ | 3,5-2F | 3,5-2CH$_3$ | 3,4,5-3F | 3-NHCOCH$_3$ |
| 4-Cl | 2-OC$_2$H$_5$ | 2-CO$_2$C$_2$H$_5$ | 2,3-2Cl | 2,3-2C$_2$H$_5$ | 2,3,4-3Cl | 4-NHCOCH$_3$ |
| 2-Br | 3-OC$_2$H$_5$ | 3-CO$_2$C$_2$H$_5$ | 2,4-2Cl | 2,4-2C$_2$H$_5$ | 2,3,5-3Cl | 2-NHSO$_2$CH$_3$ |
| 3-Br | 4-OC$_2$H$_5$ | 4-CO$_2$C$_2$H$_5$ | 2,5-2Cl | 2,5-2C$_2$H$_5$ | 2,3,6-3Cl | 3-NHSO$_2$CH$_3$ |
| 4-Br | 2-COCH$_3$ | 2-N(CH$_3$)$_2$ | 2,6-2Cl | 2,6-2C$_2$H$_5$ | 2,4,5-3Cl | 4-NHSO$_2$CH$_3$ |
| 2-I | 3-COCH$_3$ | 3-N(CH$_3$)$_2$ | 3,4-2Cl | 3,4-2C$_2$H$_5$ | 2,4,6-3Cl | 2-(Ph-4-Cl) |
| 3-I | 4-COCH$_3$ | 4-N(CH$_3$)$_2$ | 3,5-2Cl | 3,5-2C$_2$H$_5$ | 3,4,5-3Cl | 3-(Ph-4-Cl) |
| 4-I | 2-CH$_2$Ph | 2-N(C$_2$H$_5$)$_2$ | 2,3-2Br | 2,3-2CF$_3$ | 2,3,4-3Br | 4-(Ph-4-Cl) |
| 2-CH$_3$ | 3-CH$_2$Ph | 3-N(C$_2$H$_5$)$_2$ | 2,4-2Br | 2,4-2CF$_3$ | 2,3,5-3Br | 2-CH(CH$_3$)$_2$ |
| 3-CH$_3$ | 4-CH$_2$Ph | 4-N(C$_2$H$_5$)$_2$ | 2,5-2Br | 2,5-2CF$_3$ | 2,3,6-3Br | 3-CH(CH$_3$)$_2$ |
| 4-CH$_3$ | 2-C(CH$_3$)$_3$ | 4-Ph | 2,6-2Br | 2,6-2CF$_3$ | 2,4,5-3Br | 4-CH(CH$_3$)$_2$ |
| 2-C$_2$H$_5$ | 3-C(CH$_3$)$_3$ | 2-OPh | 3,4-2Br | 3,4-2CF$_3$ | 2,4,6-3Br | 2-CF$_3$-4-Cl |
| 3-C$_2$H$_5$ | 4-C(CH$_3$)$_3$ | 3-OPh | 3,5-2Br | 3,5-2CF$_3$ | 3,4,5-3Br | 2-CF$_3$-4-Br |
| 4-C$_2$H$_5$ | 2-COCH$_3$ | 4-OPh | 2,3-2CN | 2,6-2SCF$_3$ | 4-CH$_3$-3-F | 3-CF$_3$-4-NO$_2$ |
| 2-CF$_3$ | 3-COCH$_3$ | 2,3-2OCH$_3$ | 2,4-2CN | 3,4-2SCF$_3$ | 4-CH$_3$-3-Cl | 3-CF$_3$-4-F |
| 3-CF$_3$ | 4-COCH$_3$ | 2,4-2OCH$_3$ | 2,5-2CN | 3,5-2SCF$_3$ | 4-CH$_3$-3-Br | 3-CF$_3$-4-Cl |
| 4-CF$_3$ | 2-COC$_2$H$_5$ | 2,5-2OCH$_3$ | 2,6-2CN | 2,3-2SCH$_3$ | 2,4,6-3CF$_3$ | 4-CF$_3$-2-NO$_2$ |
| 2-OCH$_3$ | 3-COC$_2$H$_5$ | 2,6-2OCH$_3$ | 3,4-2CN | 2,4-2SCH$_3$ | 2-CH$_3$-3-F | 4-CF$_3$-2-Cl |
| 3-OCH$_3$ | 4-COC$_2$H$_5$ | 3,4-2OCH$_3$ | 3,5-2CN | 2,5-2SCH$_3$ | 2-CH$_3$-3-Cl | 4-CF$_3$-2-Br |
| 4-OCH$_3$ | 2-SOCH$_3$ | 3,5-2OCH$_3$ | 2-F-4-Cl | 2,6-2SCH$_3$ | 2-CH$_3$-4-F | 2-CH$_3$-5-NO$_2$ |
| 2-SCH$_3$ | 3-SOCH$_3$ | 3-CONH$_2$ | 2-F-4-Br | 3,4-2SCH$_3$ | 2-CH$_3$-4-Cl | 2-CH$_3$-3-NO$_2$ |
| 3-SCH$_3$ | 4-SOCH$_3$ | 4-CONH$_2$ | 2-F-4-I | 3,5-2SCH$_3$ | 2-CH$_3$-4-Br | 2-SCH$_3$-5-Cl |
| 4-SCH$_3$ | 2-SO$_2$CH$_3$ | 2-OCH$_2$Ph | 2-F-5-Cl | 2,3-2OCF$_3$ | 2-CH$_3$-5-F | 4-SO$_2$CH$_3$-2-Cl |
| 2-OCF$_3$ | 3-SO$_2$CH$_3$ | 3-OCH$_2$Ph | 3-F-5-Cl | 2,4-2OCF$_3$ | 2-CH$_3$-5-Cl | 2-CH$_3$-4-NO$_2$ |
| 3-OCF$_3$ | 4-SO$_2$CH$_3$ | 4-OCH$_2$Ph | 4-F-5-Cl | 2,5-2OCF$_3$ | 2-CH$_3$-5-Br | 2-CH$_3$-4-OCH$_3$ |
| 4-OCF$_3$ | 2-SOC$_2$H$_5$ | 2,3-2NO$_2$ | 4-F-6-Cl | 2,6-2OCF$_3$ | 2-CH$_3$-6-Cl | 2-CH$_3$-4-C$_2$H$_5$ |
| 2-CN | 3-SOC$_2$H$_5$ | 2,4-2NO$_2$ | 2,3,4-3F | 3,4-2OCF$_3$ | 3-CH$_3$-2-Br | 2-CH$_3$-6-NO$_2$ |
| 3-CN | 4-SOC$_2$H$_5$ | 2,5-2NO$_2$ | 2,3,5-3F | 3,5-2OCF$_3$ | 3-CH$_3$-4-Cl | 2,4,6-3NO$_2$ |
| 4-CN | 2-OCHF$_2$ | 2,6-2NO$_2$ | 2,3,6-3F | 2,3-2SCF$_3$ | 3-CH$_3$-4-Br | 2,3-2Cl-4-Br |

| R | R | R | R | R |
|---|---|---|---|---|
| 3-OCHF$_2$ | 3,4-2NO$_2$ | 2,4,5-3F | 2,4-2SCF$_3$ | 3-CH$_3$-4-I |
| 4-OCHF$_2$ | 3,5-2NO$_2$ | 2,4,6-3F | 2,5-2SCF$_3$ | 2-CH$_3$-4-I |
| 5-CF$_3$-2-Cl | 5-CF$_3$-2-OCH$_3$ | 4-CH$_3$-2,6-2Br | 3-CH$_3$-4-NHCOCH$_3$ | 2-NO$_2$-4-F |
| 5-CF$_3$-2-Br | 2-CF$_3$-4-NO$_2$ | 5-CH$_3$-4-F-6-Cl | 4-CH$_3$-3-NHSO$_2$CH$_3$ | 2-NO$_2$-4-Cl |
| 2-CN-3-F | 2,4-2NO$_2$-6-Cl | 4-C(CH$_3$)$_3$-2-Cl | 4-CH$_3$-3-OCH$_2$Ph-6-Br | 2-NO$_2$-4-Br |
| 2-CN-3-Cl | 2,4-2NO$_2$-6-Br | 4-CF$_3$-2-Cl-6-Br | 5-CH$_3$-2-OCH$_3$-4-Cl | 2-NO$_2$-5-Cl |
| 2-CN-4-NO$_2$ | 2,3-2CH(CH$_3$)$_2$ | 2-COOCH$_3$-4-Br | 4-COCH$_3$-2,6-2Cl | 3-NO$_2$-4-Cl |
| 2-CN-4-Cl | 2,4-2CH(CH$_3$)$_2$ | 4-COOCH$_3$-2-Cl | 5-CF$_3$-2-NHCOCH$_3$ | 3-NO$_2$-4-Br |
| 2-CN-4-Br | 2,5-2CH(CH$_3$)$_2$ | 4-COOCH$_3$-2-Br | 2-CH$_3$-4-NO$_2$-6-Cl | 4-NO$_2$-2-Cl |
| 4-CN-2-CF$_3$ | 2,6-2CH(CH$_3$)$_2$ | 2,4,6-3CH(CH$_3$)$_2$ | 2-CH$_3$-4-NO$_2$-6-Br | 5-NO$_2$-2-Cl |
| 4-CN-2-Cl | 3,4-2CH(CH$_3$)$_2$ | 2,4,6-3C(CH$_3$)$_3$ | 2-CH$_3$-6-NO$_2$-4-Cl | 5-NO$_2$-2-Br |
| 4-CN-2-NO$_2$ | 3,5-2CH(CH$_3$)$_2$ | 2,3-2CH$_3$-6-NO$_2$ | 2-CH$_3$-6-NO$_2$-4-Br | 2-OCH$_3$-5-Cl |
| 5-CH$_3$-2-F | 2-NO$_2$-4-OCH$_3$ | 2,4-2OCH$_3$-5-Cl | 2,5-2OCH$_3$-4-NO$_2$ | 4-OCH$_3$-3-F |
| 4-CH$_3$-2-NO$_2$ | 2-NO$_2$-4-OC$_2$H$_5$ | 5-CONH$_2$-2-Cl | 2,6-2CH$_3$-4-C(CH$_3$)$_3$ | 4-OCH$_3$-3-Cl |

TABLE 1-continued

| | | | | |
|---|---|---|---|---|
| 4-CH$_3$-3-NO$_2$ | 2,3-2C(CH$_3$)$_3$ | 4-N(CH$_3$)2-2-NO$_2$ | 4-CF$_3$-2-NO$_2$-5-Cl | 3-NO$_2$-4-F |
| 5-CH$_3$-2-CN | 2,4-2C(CH$_3$)$_3$ | 5-N(CH$_3$)2-2-NO$_2$ | 4-CF$_3$-2-NO$_2$-6-Cl | 2-OCF$_3$-4-CN |
| 5-NO$_2$-2-F | 2,5-2C(CH$_3$)$_3$ | 4,5-2CH$_3$-2-NO$_2$ | 4-CF$_3$-2-NO$_2$-6-Br | 2-OCF$_3$-4-Cl |
| 2-CF$_3$-4,6-2Cl | 2,6-2C(CH$_3$)$_3$ | 2-NO$_2$-4-F-5-Cl | 5-CH$_3$-2-CONH$_2$ | 2-OCF$_3$-4-Br |
| 2-CF$_3$-4,6-2Br | 3,4-2C(CH$_3$)$_3$ | 2-CN-4-NO$_2$-6-Cl | 2-CH$_3$-5-CONH$_2$ | 2-F-4,6-2Br |
| 3-CH$_3$-2,6-2Cl | 3,5-2C(CH$_3$)$_3$ | 2-CN-4-NO$_2$-6-Br | 2,4-2F-6-Cl | 4-OCF$_3$-2-Cl |
| 2-CH$_3$-4,6-2Br | 4-SO$_2$NH$_2$ | 2-OCH$_2$CH=CH$_2$ | 4-O(CH$_2$)$_2$N(CH$_3$)$_2$ | 4-OCF$_3$-2-Br |
| 2,4,6-3OCH$_3$ | 4-NO$_2$-2-OCH$_3$ | 3-OCH$_2$CH=CH$_2$ | 4-CH$_3$-3-OCH$_2$Ph | 2,3,5,6-4F |
| 3,4,5-3OCH$_3$ | 2-CH$_2$CH=CH$_2$ | 4-OCH$_2$CH=CH$_2$ | 2-CH$_2$C(CH$_3$)=CH$_2$ | 2-CN-4,6-2Cl |
| 2,4,6-3SCH$_3$ | 3-CH$_2$CH=CH$_2$ | 2-OCH$_2$C≡CH | 3-CH$_2$C(CH$_3$)=CH$_2$ | 2-CN-4,6-2Br |
| 2,4,6-3OCF$_3$ | 4-CH$_2$CH=CH$_2$ | 3-OCH$_2$C≡CH | 4-CH$_2$C(CH$_3$)=CH$_2$ | 4-CN-2,6-2Cl |
| 2,4,6-3SCF$_3$ | 2-C(CH$_3$)=CH$_2$ | 4-OCH$_2$C≡CH | 4-O(CH$_2$)$_3$CH$_3$-2-NO$_2$ | 4-CF$_3$-2,6-2Cl |
| 2-CH$_2$C≡CH | 3-C(CH$_3$)=CH$_2$ | 5-NO$_2$-2-OCH$_3$ | 3-OCH$_3$-4-CO$_2$CH$_3$ | 4-CF$_3$-2,6-2Br |
| 3-CH$_2$C≡CH | 4-C(CH$_3$)=CH$_2$ | 5-CH$_3$-2-OCH$_3$ | 2-CH(CH$_3$)CH$_2$CH(CH$_3$)$_2$ | 2,3,4,5-5Cl |
| 4-CH$_2$C≡CH | 4-F-2,6-2Br | 4-NO$_2$-2,6-2Cl | 2,3-(CH$_2$CH$_2$CH$_2$—) | 2,3-(OCF$_2$O—) |
| 2-F-3-Cl | 2,4-2F-6-Cl | 4-OCF$_3$-2-NO$_2$ | 2,3-(CH$_2$CH$_2$CH$_2$CH$_2$—) | 2,3-(OCH$_2$O—) |
| 3-CH3-2-Cl | 2-F-4-Cl-6-Br | 6-NO$_2$-2,3,4-3F | 4-NO$_2$-2,5-2Cl | 3,4-(OCH$_2$O—) |
| 4-O(CH$_2$)$_3$CH$_3$ | 2,3,5,6-4F-4-CF$_3$ | 4-NO$_2$-2,6-2Br | 4-F-3-Cl-2,6-2Br | 3,4-(OCF$_2$O—) |
| 4-Ph | 4-(4-Cl—Ph) | 2-Ph | 3-Ph | 4-(4-Br—Ph) |
| 4-(4-F-Ph) | 4-(4-CH$_3$—Ph) | 4-(4-OCH$_3$—Ph) | 4-(4-CF$_3$—Ph) | 4-(4-CN—Ph) |
| 4-(4-NO$_2$-Ph) | 4-(2-CH$_3$—Ph) | 4-(2-Cl—Ph) | 4-(3-Cl—Ph) | 4-OPh |
| 4-O(Ph-4-Cl) | 4-O(Ph-4-Br) | 4-O(Ph-4-F) | 4-O(Ph-4-CH$_3$) | 2-OPh |

TABLE 2

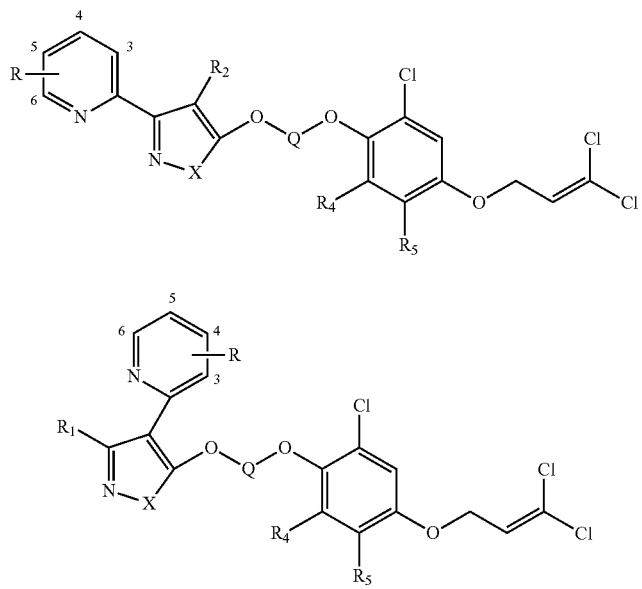

| R | R | R | R | R |
|---|---|---|---|---|
| H | 3-Br | 6-OCH$_3$ | 3-CH$_3$-5-NO$_2$ | 6-CH$_3$-3,5-2Br |
| 3-CH$_3$ | 4-Br | 5-OCH$_3$ | 4-CH$_3$-3-NO$_2$ | 3-CONH$_2$-4,6-2Cl |
| 4-CH$_3$ | 5-Br | 3,5-2Cl | 4-CH$_3$-5-NO$_2$ | 4-CH$_3$-5-NO$_2$-3-Br |
| 5-CH$_3$ | 6-Br | 3,5-2Br | 5-CH$_3$-3-NO$_2$ | 3-CN-4,6-2Cl |
| 6-CH$_3$ | 5-I | 4-CH$_3$-5-Br | 6-CH$_3$-4-NO$_2$ | 3-CN-4-CH$_3$-6-Cl |
| 3-Cl | 5-F | 6-CH$_3$-5-CN | 6-CH$_3$-5-NO$_2$ | 3-CN-4-CF$_3$-6-Cl |
| 4-Cl | 6-F | 3,5,6-3Cl | 3-NO$_2$-5-Cl | 4-CH$_3$-5-CN-6-Cl |
| 5-Cl | 3-CN | 3-CO$_2$CH$_3$ | 3-NO$_2$-5-Br | 4-CF$_3$-5-CN-6-Cl |
| 6-Cl | 4-CN | 5-CO$_2$CH$_3$ | 5-NO$_2$-3-Br | 3-CO$_2$CH$_3$-6-Cl |
| 3-CF$_3$ | 5-CN | 3-OCH$_2$Ph | 5-CH$_3$-3-Br | 5-CO$_2$CH$_3$-6-Cl |
| 4-CF$_3$ | 6-CN | 5-CF$_3$-3-Cl | 6-CH$_3$-5-Br | 5-CF$_3$-3,6-2Cl |
| 5-CF$_3$ | 3-NO$_2$ | 5-CN-3-Cl | 3-CH$_3$-5-Br | 5-CF$_3$-6-Cl |
| 6-CF$_3$ | 5-NO$_2$ | 5-CH$_3$-3-Cl | 3-CF$_3$-6-Cl | 3-CN-6-Cl |

TABLE 3
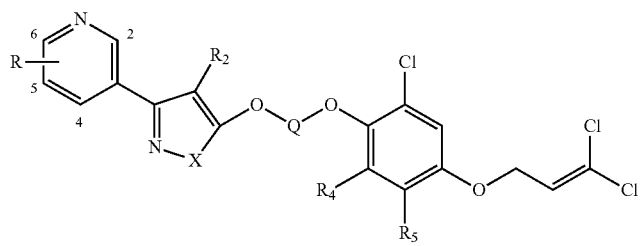
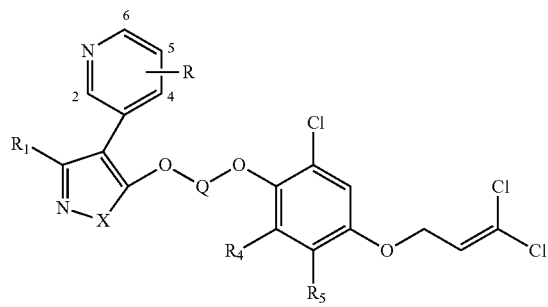
| R | R | R | R | R |
|---|---|---|---|---|
| H | 2-OCH₃ | 4-CH₃-2-Cl | 4-CF₃-2,6-2Cl | 6-OPh-3,5-2CH₃-4-Cl |
| 2-Cl | 6-OCH₃ | 5-CH₃-2-Cl | 4-CH₃-2,6-2Cl | 6-OCH₃-2-Cl |
| 6-Cl | 6-OPh | 6-CH₃-2-Cl | 4-CF₃-2,6-2Cl | 6-OPh-4-Br |
| 2-Br | 2,6-2Cl | 2-OPh-6-Cl | 2-OCH₂CF₃ | 6-NHCH₃-5-Cl |
| | | | | 6-SO₂CH₃-5-Cl |
| 6-Br | 5,6-2Cl | 6-SPh-2,5-2Cl | 4-CH₃ | |
| 6-Ph | 2,5-2Cl | 4-CF₃ | 6-CF₃ | 2-N⟨morpholino⟩ |
TABLE 4
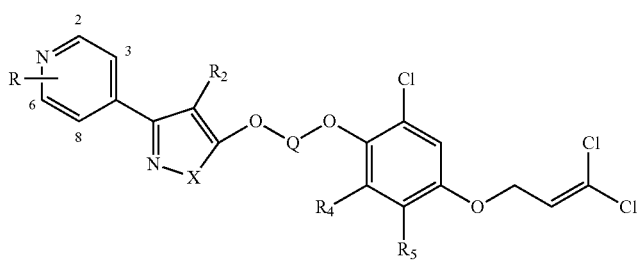
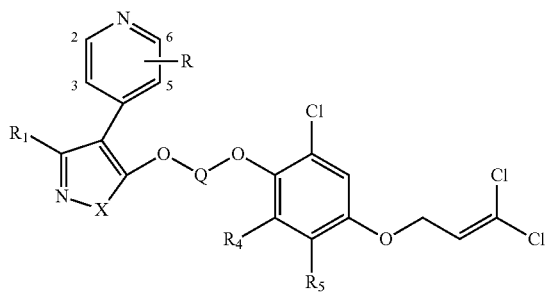
| R | R | R | R | R |
|---|---|---|---|---|
| H | 3-Cl | 2-OCH₃ | 2,6-2Cl | 2-OCH₃-6-Cl |
| 2-Cl | 2-Br | 2,6-2OCH₃ | 6-OPh | 2-NHCH₃-6-Cl |

TABLE 5

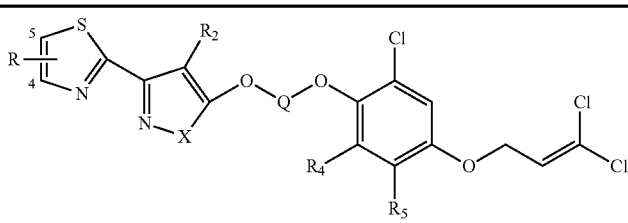

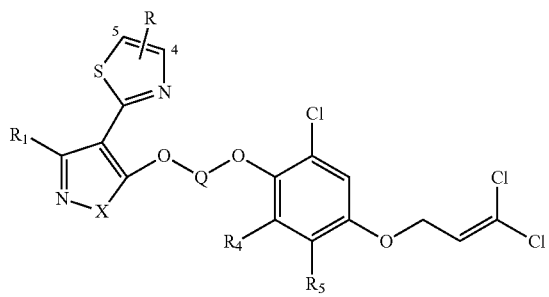

| R | R | R | R | R |
|---|---|---|---|---|
| H | 5-NO₂ | 4-CO₂C₂H₅ | 4-CH₃-5-COCH₃ | 4-(Ph-4-Cl)-5-CO₂C₂H₅ |
| 5-Cl | 5-OPh | 4-(Ph-3,4-2F) | 4-CH₃-5-CO₂C₂H₅ | 4,5-(CCl=CH—CH=CH—) |
| 5-CH₃ | 5-OCH₃ | 4-(Ph-4-Cl) | 4-CF₃-5-CO₂C₂H₅ | 4,5-(CH=CCl—CH=CH—) |
| 4-Cl | 4,5-2Cl | 4,5-(CH₂—)₃ | 5-CH₃-4-CO₂C₂H₅ | 4,5-(CH=CH—CCl=CH—) |
| 5-Br | 4,5-2CH₃ | 4,5-(CH₂—)₄ | 5-Ph-4-CO₂C₂H₅ | 4,5-(CMe=CH—CH=CH—) |
| 4-CH₃ | 4-C(CH₃)₃ | 4-CF₃-5-CN | 4-CH₃-5-CONHCH₃ | 4,5-(CH=CMe—CH=CH—) |
| 5-Ph | 5-(Ph-4-Cl) | 4-CH₂CO₂C₂H₅ | 4-CF₃-5-CONHCH₃ | 4,5-(C(OMe)=CH—CH=CH—) |
| 4-Ph | 4-(Ph-4-Br) | 4-Ph-5-CO₂C₂H₅ | 4,5-(CH=CH—CH=CH—) | 4,5-(CH=C(OMe)—CH=CH—) |

TABLE 6

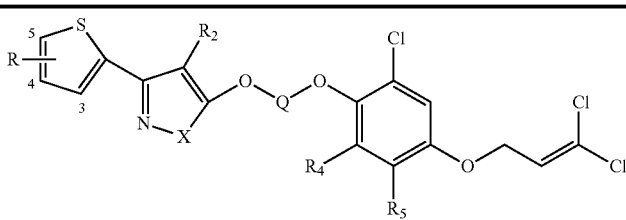

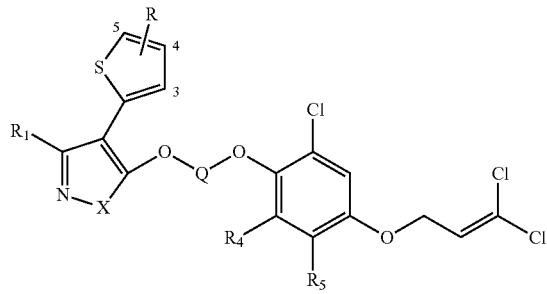

| R | R | R | R | R |
|---|---|---|---|---|
| H | 5-NO₂ | 4-CO₂C₂H₅ | 4-CH₃-5-COCH₃ | 4-(Ph-4-Cl)-5-CO₂C₂H₅ |
| 5-Cl | 5-OPh | 4-(Ph-3,4-2F) | 4-CH₃-5-CO₂C₂H₅ | 4,5-(CCl=CH—CH=CH—) |
| 5-CH₃ | 5-OCH₃ | 4-(Ph-4-Cl) | 4-CF₃-5-CO₂C₂H₅ | 4,5-(CH=CCl—CH=CH—) |
| 4-Cl | 4,5-2Cl | 4,5-(CH₂—)₃ | 5-CH₃-4-CO₂C₂H₅ | 4,5-(CH=CH—CCl=CH—) |
| 3-Cl | 3-CH₃ | 3-OCH₃ | 3-NO₂ | 3,4-2CH₃ |
| 5-Br | 4,5-2CH₃ | 4,5-(CH₂—)₄ | 5-Ph-4-CO₂C₂H₅ | 4,5-(CMe=CH—CH=CH—) |
| 3-Br | 3-Ph | 3-OPh | 3,5-2CH₃ | 3-CH₃-5-COCH₃ |
| 3-(Ph-4-Cl) | 3-(Ph-3,4-2F) | 3-CO₂C₂H₅ | 3-CF₃-5-CN | 3-CH₂CO₂C₂H₅ |
| 4-CH₃ | 4-C(CH₃)₃ | 4-CF₃-5-CN | 4-CH₃-5-CONHCH₃ | 4,5-(CH=CMe—CH=CH—) |
| 3-CF₃-5-CO₂C₂H₅ | 3-COCH₃-4-CH₃ | 3-CO₂C₂H₅-4-CF₃ | 3,4-(CH=CH—CH=CH—) | 3,4-(CH₂—)₄ |
| 5-Ph | 5-(Ph-4-Cl) | 4-CH₂CO₂C₂H₅ | 4-CF₃-5-CONHCH₃ | 4,5-(C(OMe)=CH—CH=CH—) |
| 4-Ph | 4-(Ph-4-Br) | 4-Ph-5-CO₂C₂H₅ | 4,5-(CH=CH—CH=CH—) | 4,5-(CH=C(OMe)—CH=CH—) |

TABLE 7

| R | R | R | R | R |
|---|---|---|---|---|
| H | 5-NO$_2$ | 4-CO$_2$C$_2$H$_5$ | 4-CH$_3$-5-COCH$_3$ | 4-(Ph-4-Cl)-5-CO$_2$C$_2$H$_5$ |
| 5-Cl | 5-OPh | 4-(Ph-3,4-2F) | 4-CH$_3$-5-CO$_2$C$_2$H$_5$ | 4,5-(CCl=CH—CH=CH—) |
| 5-CH$_3$ | 5-OCH$_3$ | 4-(Ph-4-Cl) | 4-CF$_3$-5-CO$_2$C$_2$H$_5$ | 4,5-(CH=CCl—CH=CH—) |
| 4-Cl | 4,5-2Cl | 4,5-(CH$_2$—)$_3$ | 5-CH$_3$-4-CO$_2$C$_2$H$_5$ | 4,5-(CH=CH—CCl=CH—) |
| 2-Cl | 2-CH$_3$ | 2-OCH$_3$ | 2-NO$_2$ | 2,4-2CH$_3$ |
| 5-Br | 4,5-2CH$_3$ | 4,5-(CH$_2$—)$_4$ | 5-Ph-4-CO$_2$C$_2$H$_5$ | 4,5-(CMe=CH—CH=CH—) |
| 2-Br | 2-Ph | 2-OPh | 2,5-2CH$_3$ | 2-CH$_3$-5-COCH$_3$ |
| 2-(Ph-4-Cl) | 2-(Ph-3,4-2F) | 2-CO$_2$C$_2$H$_5$ | 2-CF$_3$-5-CN | 2-CH$_2$CO$_2$C$_2$H$_5$ |
| 4-CH$_3$ | 4-C(CH$_3$)$_3$ | 4-CF$_3$-5-CN | 4-CH$_3$-5-CONHCH$_3$ | 4,5-(CH=CMe—CH=CH—) |
| 2-CF$_3$-5-CO$_2$C$_2$H$_5$ | 2-COCH$_3$-4-CH$_3$ | 2-CO$_2$C$_2$H$_5$-4-CF$_3$ | 2,5-2Cl | 2,4-2Cl |
| 5-Ph | 5-(Ph-4-Cl) | 4-CH$_2$CO$_2$C$_2$H$_5$ | 4-CF$_3$-5-CONHCH$_3$ | 4,5-(C(OMe)=CH—CH=CH—) |
| 4-Ph | 4-(Ph-4-Br) | 4-Ph-5-CO$_2$C$_2$H$_5$ | 4,5-(CH=CH—CH=CH—) | 4,5-(CH=C(OMe)—CH=CH—) |

TABLE 8

| R$_1$ | R$_1$ | R$_1$ | R$_1$ | R$_1$ |
|---|---|---|---|---|
| H | (CH$_2$)$_2$CH$_3$ | (CH$_2$)$_6$CH$_3$ | CF$_2$CF$_3$ | CH$_2$CO$_2$CH$_3$ |
| CH$_3$ | CH(CH$_3$)$_2$ | (CH$_2$)$_2$CH$_3$ | CH$_2$CH$_2$Cl | CH$_2$CO$_2$C$_2$H$_5$ |
| C$_2$H$_5$ | (CH$_2$)$_3$CH$_3$ | CH$_2$CN | CH$_2$CH$_2$Br | CH$_2$C(CH$_3$)$_2$CH$_3$ |
| cyclopropyl | cyclopentylmethyl | cyclohexylmethyl | CH$_2$C(CH$_3$)$_3$ | CH$_2$CH$_2$C(CH$_3$)$_3$ |
| C(CH$_3$)$_3$ | (CH$_2$)$_3$CH$_3$ | CF$_3$ | CH(CH$_3$)CH$_2$CH(CH$_3$)$_2$ | CH(CH$_3$)CH$_2$CH$_3$ |
| CH$_2$CH$_2$CN | (CH$_2$)$_4$CH$_3$ | CH$_2$CF$_3$ | CH$_2$CHF$_2$ | CH$_2$CH(CH$_3$)$_2$ |

TABLE 9

| R₂ | R₂ | R₂ | R₂ | R₂ |
|---|---|---|---|---|
| H | CH₃ | (CH₂)₆CH₃ | CH₂CHF₂ | CH₂CO₂CH₃ |
| Cl | C₂H₅ | (CH₂)₇CH₃ | OCF₃ | CH₂CO₂C₂H₅ |
| Br | (CH₂)₂CH₃ | CF₃ | OCH₃ | CH₂C(CH₃)₂CH₃ |
| F | CH(CH₃)₂ | CH₂CF₃ | OC₂H₅ | CH₂CH₂C(CH₃)₃ |
| I | (CH₂)₃CH₃ | CF₂CF₃ | OC(CH₃)₃ | CH(CH₃)CH₂CH₃ |
| cyclopropyl | cyclopentyl | cyclohexyl | OCH₂CF₃ | CH₂CH(CH₃)₂ |
| C(CH₃)₃ | (CH₂)₅CH₃ | CH₂CH₂Br | OCH(CH₃)₂ | CH(CH₃)CH₂CH(CH₃)₂ |
| CH₂CH₂Cl | (CH₂)₄CH₃ | CH₂C(CH₃)₃ | OCH₂CH₂Cl | OCH₂CH₂CH₃ |
| SCF₃ | SC₂H₅ | SCH₂CF₃ | SCH₂CH₂Cl | SCH(CH₃)₂ |
| SCH₃ | SC(CH₃)₃ | OPh-2-Cl | OPh | CH₂Ph-4-F |
| OPh-4-F | CH₂Ph | OPh-4-Cl | CH₂Ph-4-Cl | OPh-4-Cl |
| CH₂Ph-4-CH₃ | CH₂Ph-4-C₂H₅ | CH₂Ph-2-Cl | CH₂Ph-2-CH₃ | OPh-2-CH₃ |
| OPh-4-CH₃ | OPh-4-C₂H₅ | CH₂Ph-3-Cl | CH₂Ph-3-F | OPh-3-Cl |

The present invention is also explained by the following compounds in Tables 10-12, but without being restricted thereby.

TABLE 10

I-1

| No. | X | R₁ | R₂ | R₄ | R₅ | Q |
|---|---|---|---|---|---|---|
| 1 | NCH₃ | C₆H₅ | H | Cl | H | —CH₂CH₂CH₂— |
| 2 | NCH₃ | 4-Cl—C₆H₄ | H | Cl | H | —CH₂CH₂CH₂— |
| 3 | NCH₃ | 4-F—C₆H₄ | H | Cl | H | —CH₂CH₂CH₂— |
| 4 | NCH₃ | 4-NO₂—C₆H₄ | H | Cl | H | —CH₂CH₂CH₂— |
| 5 | NCH₃ | 4-CF₃—C₆H₄ | H | Cl | H | —CH₂CH₂CH₂— |
| 6 | NCH₃ | 4-CN—C₆H₄ | H | Cl | H | —CH₂CH₂CH₂— |
| 7 | NCH₃ | 4-CH₃CO₂—C₆H₄ | H | Cl | H | —CH₂CH₂CH₂— |
| 8 | NCH₃ | 4-CH₃S—C₆H₄ | H | Cl | H | —CH₂CH₂CH₂— |
| 9 | NCH₃ | 4-CH₃SO₂—C₆H₄ | H | Cl | H | —CH₂CH₂CH₂— |
| 10 | NCH₃ | 4-CF₃O—C₆H₄ | H | Cl | H | —CH₂CH₂CH₂— |
| 11 | NCH₃ | 2,4-2Cl—C₆H₃ | H | Cl | H | —CH₂CH₂CH₂— |
| 12 | NCH(CH₃)₂ | 4-Cl—C₆H₄ | H | Cl | H | —CH₂CH₂CH₂— |
| 13 | NCH₃ | 4-CH₃O—C₆H₄ | H | Cl | H | —CH₂CH₂CH₂— |
| 14 | NCH₃ | 2-Cl-4-F—C₆H₃ | H | Cl | H | —CH₂CH₂CH₂— |
| 15 | NCH₃ | 3-Cl—C₆H₄ | H | Cl | H | —CH₂CH₂CH₂— |
| 16 | NCH₃ | 4-Br—C₆H₄ | H | Cl | H | —CH₂CH₂CH₂— |
| 17 | NCH₃ | 4-CH₃—C₆H₄ | H | Cl | H | —CH₂CH₂CH₂— |
| 18 | NCH₃ | 4-C₂H₅—C₆H₄ | H | Cl | H | —CH₂CH₂CH₂— |
| 19 | NCH₃ | 4-CF₃CH₂O—C₆H₄ | H | Cl | H | —CH₂CH₂CH₂— |
| 20 | NCH₃ | 4-PhO—C₆H₄ | H | Cl | H | —CH₂CH₂CH₂— |
| 21 | NCH₃ | 2-Cl—C₆H₄ | H | Cl | H | —CH₂CH₂CH₂— |
| 22 | NCH₃ | 3,4-2CH₃O—C₆H₃ | H | Cl | H | —CH₂CH₂CH₂— |
| 23 | NCH₃ | 3,5-2Cl—C₆H₃ | H | Cl | H | —CH₂CH₂CH₂— |
| 24 | NCH₃ | 2-CH₃O—C₆H₄ | H | Cl | H | —CH₂CH₂CH₂— |
| 25 | NCH₃ | 2,5-2CH₃-Thiophen-3-yl | H | Cl | H | —CH₂CH₂CH₂— |
| 26 | NCH₃ | 2,4-2CH₃—C₆H₃ | H | Cl | H | —CH₂CH₂CH₂— |

TABLE 10-continued

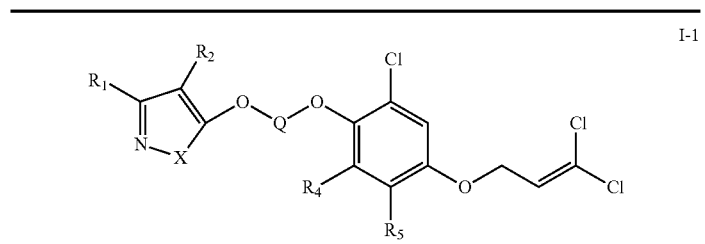

I-1

| No. | X | R₁ | R₂ | R₄ | R₅ | Q |
|---|---|---|---|---|---|---|
| 27 | NCH₃ | 3,4-2CH₃—C₆H₃ | H | Cl | H | —CH₂CH₂CH₂— |
| 28 | NCH₃ | 2,5-2CH₃—C₆H₃ | H | Cl | H | —CH₂CH₂CH₂— |
| 29 | NCH₃ | 2,6-2CH₃—C₆H₃ | H | Cl | H | —CH₂CH₂CH₂— |
| 30 | NCH₃ | 6-CH₃O-Pyridin-3-yl | H | Cl | H | —CH₂CH₂CH₂— |
| 31 | NCH₃ | 6-CF₃CH₂O-Pyridin-3-yl | H | Cl | H | —CH₂CH₂CH₂— |
| 32 | NCH₃ | 4-(4-Cl—Ph)—C₆H₄ | H | Cl | H | —CH₂CH₂CH₂— |
| 33 | NCH₃ | Thiophen-2-yl | H | Cl | H | —CH₂CH₂CH₂— |
| 34 | NCH₃ | 5-Cl-Thiophen-2-yl | H | Cl | H | —CH₂CH₂CH₂— |
| 35 | NCH₃ | Thiazol-2-yl | H | Cl | H | —CH₂CH₂CH₂— |
| 36 | NCH₃ | Furan-2-yl | H | Cl | H | —CH₂CH₂CH₂— |
| 37 | NCH₃ | 4-i-C₃H₇—C₆H₄ | H | Cl | H | —CH₂CH₂CH₂— |
| 38 | NCH₃ | 4-n-C₃H₇—C₆H₄ | H | Cl | H | —CH₂CH₂CH₂— |
| 39 | NCH₃ | 4-t-C₄H₉—C₆H₄ | H | Cl | H | —CH₂CH₂CH₂— |
| 40 | NCH₃ | 2,4,6-3CH₃—C₆H₂ | H | Cl | H | —CH₂CH₂CH₂— |
| 41 | NCH₃ | 2,4,6-3Cl—C₆H₂ | H | Cl | H | —CH₂CH₂CH₂— |
| 42 | NCH₃ | C₆H₅ | Cl | Cl | H | —CH₂CH₂CH₂— |
| 43 | NCH₃ | 4-Cl—C₆H₄ | Cl | Cl | H | —CH₂CH₂CH₂— |
| 44 | NCH₃ | 4-F—C₆H₄ | Cl | Cl | H | —CH₂CH₂CH₂— |
| 45 | NCH₃ | 4-NO₂—C₆H₄ | Cl | Cl | H | —CH₂CH₂CH₂— |
| 46 | NCH₃ | 4-CF₃—C₆H₄ | Cl | Cl | H | —CH₂CH₂CH₂— |
| 47 | NCH₃ | 4-CN—C₆H₄ | Cl | Cl | H | —CH₂CH₂CH₂— |
| 48 | NCH₃ | 4-CH₃CO₂—C₆H₄ | Cl | Cl | H | —CH₂CH₂CH₂— |
| 49 | NCH₃ | 4-CH₃S—C₆H₄ | Cl | Cl | H | —CH₂CH₂CH₂— |
| 50 | NCH₃ | 4-CH₃SO₂—C₆H₄ | Cl | Cl | H | —CH₂CH₂CH₂— |
| 51 | NCH₃ | 4-CF₃O—C₆H₄ | Cl | Cl | H | —CH₂CH₂CH₂— |
| 52 | NCH₃ | 2,4-2Cl—C₆H₃ | Cl | Cl | H | —CH₂CH₂CH₂— |
| 53 | NCH(CH₃)₂ | 4-Cl—C₆H₄ | Cl | Cl | H | —CH₂CH₂CH₂— |
| 54 | NCH₃ | 4-CH₃O—C₆H₄ | Cl | Cl | H | —CH₂CH₂CH₂— |
| 55 | NCH₃ | 2-Cl-4-F-C₆H₃ | Cl | Cl | H | —CH₂CH₂CH₂— |
| 56 | NCH₃ | 3-Cl—C₆H₄ | Cl | Cl | H | —CH₂CH₂CH₂— |
| 57 | NCH₃ | 4-Br—C₆H₄ | Cl | Cl | H | —CH₂CH₂CH₂— |
| 58 | NCH₃ | 4-CH₃—C₆H₄ | Cl | Cl | H | —CH₂CH₂CH₂— |
| 59 | NCH₃ | 4-C₂H₅—C₆H₄ | Cl | Cl | H | —CH₂CH₂CH₂— |
| 60 | NCH₃ | 4-CF₃CH₂O—C₆H₄ | Cl | Cl | H | —CH₂CH₂CH₂— |
| 61 | NCH₃ | 4-PhO—C₆H₄ | Cl | Cl | H | —CH₂CH₂CH₂— |
| 62 | NCH₃ | 2-Cl—C₆H₄ | Cl | Cl | H | —CH₂CH₂CH₂— |
| 63 | NCH₃ | 3,4-2CH₃O—C₆H₃ | Cl | Cl | H | —CH₂CH₂CH₂— |
| 64 | NCH₃ | 3,5-2Cl—C₆H₃ | Cl | Cl | H | —CH₂CH₂CH₂— |
| 65 | NCH₃ | 2-CH₃O—C₆H₄ | Cl | Cl | H | —CH₂CH₂CH₂— |
| 66 | NCH₃ | 2,5-2CH₃-Thiophen-3-yl | Cl | Cl | H | —CH₂CH₂CH₂— |
| 67 | NCH₃ | 2,4-2CH₃—C₆H₃ | Cl | Cl | H | —CH₂CH₂CH₂— |
| 68 | NCH₃ | 3,4-2CH₃—C₆H₃ | Cl | Cl | H | —CH₂CH₂CH₂— |
| 69 | NCH₃ | 2,5-2CH₃—C₆H₃ | Cl | Cl | H | —CH₂CH₂CH₂— |
| 70 | NCH₃ | 2,6-2CH₃—C₆H₃ | Cl | Cl | H | —CH₂CH₂CH₂— |
| 71 | NCH₃ | 4-i-C₃H₇—C₆H₄ | Cl | Cl | H | —CH₂CH₂CH₂— |
| 72 | NCH₃ | 4-n-C₃H₇—C₆H₄ | Cl | Cl | H | —CH₂CH₂CH₂— |
| 73 | NCH₃ | 4-t-C₄H₉—C₆H₄ | Cl | Cl | H | —CH₂CH₂CH₂— |
| 74 | NCH₃ | 2,4,6-3CH₃—C₆H₂ | Cl | Cl | H | —CH₂CH₂CH₂— |
| 75 | NCH₃ | 2,4,6-3Cl—C₆H₂ | Cl | Cl | H | —CH₂CH₂CH₂— |
| 76 | NCH₃ | C₆H₅ | CH₃ | Cl | H | —CH₂CH₂CH₂— |
| 77 | NCH₃ | 4-Cl—C₆H₄ | CH₃ | Cl | H | —CH₂CH₂CH₂— |
| 78 | NCH₃ | 4-F—C₆H₄ | CH₃ | Cl | H | —CH₂CH₂CH₂— |
| 79 | NCH₃ | 4-NO₂—C₆H₄ | CH₃ | Cl | H | —CH₂CH₂CH₂— |
| 80 | NCH₃ | 4-CF₃—C₆H₄ | CH₃ | Cl | H | —CH₂CH₂CH₂— |
| 81 | NCH₃ | 4-CN—C₆H₄ | CH₃ | Cl | H | —CH₂CH₂CH₂— |
| 82 | NCH₃ | 4-CH₃CO₂—C₆H₄ | CH₃ | Cl | H | —CH₂CH₂CH₂— |
| 83 | NCH₃ | 4-CH₃S—C₆H₄ | CH₃ | Cl | H | —CH₂CH₂CH₂— |
| 84 | NCH₃ | 4-CH₃SO₂—C₆H₄ | CH₃ | Cl | H | —CH₂CH₂CH₂— |
| 85 | NCH₃ | 4-CF₃O—C₆H₄ | CH₃ | Cl | H | —CH₂CH₂CH₂— |
| 86 | NCH₃ | 2,4-2Cl—C₆H₃ | CH₃ | Cl | H | —CH₂CH₂CH₂— |
| 87 | NCH(CH₃)₂ | 4-Cl—C₆H₄ | CH₃ | Cl | H | —CH₂CH₂CH₂— |
| 88 | NCH₃ | 4-CH₃O—C₆H₄ | CH₃ | Cl | H | —CH₂CH₂CH₂— |
| 89 | NCH₃ | 2-Cl-4-F-C₆H₃ | CH₃ | Cl | H | —CH₂CH₂CH₂— |
| 90 | NCH₃ | 3-Cl—C₆H₄ | CH₃ | Cl | H | —CH₂CH₂CH₂— |
| 91 | NCH₃ | 4-Br—C₆H₄ | CH₃ | Cl | H | —CH₂CH₂CH₂— |
| 92 | NCH₃ | 4-CH₃—C₆H₄ | CH₃ | Cl | H | —CH₂CH₂CH₂— |

TABLE 10-continued

I-1

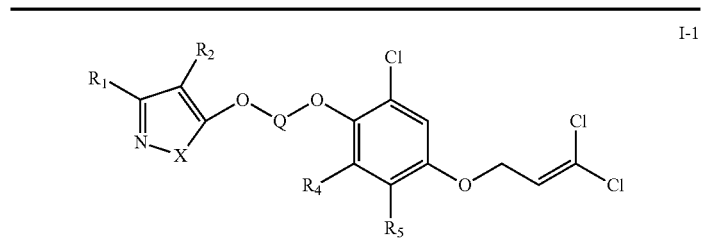

| No. | X | R₁ | R₂ | R₄ | R₅ | Q |
|---|---|---|---|---|---|---|
| 93 | NCH₃ | 4-C₂H₅—C₆H₄ | CH₃ | Cl | H | —CH₂CH₂CH₂— |
| 94 | NCH₃ | 4-CF₃CH₂O—C₆H₄ | CH₃ | Cl | H | —CH₂CH₂CH₂— |
| 95 | NCH₃ | 4-PhO—C₆H₄ | CH₃ | Cl | H | —CH₂CH₂CH₂— |
| 96 | NCH₃ | 2-Cl—C₆H₄ | CH₃ | Cl | H | —CH₂CH₂CH₂— |
| 97 | NCH₃ | 3,4-2CH₃O—C₆H₃ | CH₃ | Cl | H | —CH₂CH₂CH₂— |
| 98 | NCH₃ | 3,5-2Cl—C₆H₃ | CH₃ | Cl | H | —CH₂CH₂CH₂— |
| 99 | NCH₃ | 2-CH₃O—C₆H₄ | CH₃ | Cl | H | —CH₂CH₂CH₂— |
| 100 | NCH₃ | 2,5-2CH₃-Thiophen-3-yl | CH₃ | Cl | H | —CH₂CH₂CH₂— |
| 101 | NCH₃ | 2,4-2CH₃—C₆H₃ | CH₃ | Cl | H | —CH₂CH₂CH₂— |
| 102 | NCH₃ | 3,4-2CH₃—C₆H₃ | CH₃ | Cl | H | —CH₂CH₂CH₂— |
| 103 | NCH₃ | 2,5-2CH₃—C₆H₃ | CH₃ | Cl | H | —CH₂CH₂CH₂— |
| 104 | NCH₃ | 2,6-2CH₃—C₆H₃ | CH₃ | Cl | H | —CH₂CH₂CH₂— |
| 105 | NCH₃ | 6-CH₃O-Pyridin-3-yl | CH₃ | Cl | H | —CH₂CH₂CH₂— |
| 106 | NCH₃ | 6-CF₃CH₂O-Pyridin-3-yl | CH₃ | Cl | H | —CH₂CH₂CH₂— |
| 107 | NCH₃ | 4-(4-Cl—Ph)—C₆H₄ | CH₃ | Cl | H | —CH₂CH₂CH₂— |
| 108 | NCH₃ | Thiophen-2-yl | CH₃ | Cl | H | —CH₂CH₂CH₂— |
| 109 | NCH₃ | 5-Cl-Thiophen-2-yl | CH₃ | Cl | H | —CH₂CH₂CH₂— |
| 110 | NCH₃ | Thiazol-2-yl | CH₃ | Cl | H | —CH₂CH₂CH₂— |
| 111 | NCH₃ | Furan-2-yl | CH₃ | Cl | H | —CH₂CH₂CH₂— |
| 112 | NCH₃ | 4-i-C₃H₇—C₆H₄ | CH₃ | Cl | H | —CH₂CH₂CH₂— |
| 113 | NCH₃ | 4-n-C₃H₇—C₆H₄ | CH₃ | Cl | H | —CH₂CH₂CH₂— |
| 114 | NCH₃ | 4-t-C₄H₉—C₆H₄ | CH₃ | Cl | H | —CH₂CH₂CH₂— |
| 115 | NCH₃ | 2,4,6-3CH₃—C₆H₂ | CH₃ | Cl | H | —CH₂CH₂CH₂— |
| 116 | NCH₃ | 2,4,6-3Cl—C₆H₂ | CH₃ | Cl | H | —CH₂CH₂CH₂— |
| 117 | NCH₃ | C₆H₅ | CO₂Me | Cl | H | —CH₂CH₂CH₂— |
| 118 | NCH₃ | 4-Cl—C₆H₄ | CO₂Me | Cl | H | —CH₂CH₂CH₂— |
| 119 | NCH₃ | 4-F—C₆H₄ | CO₂Me | Cl | H | —CH₂CH₂CH₂— |
| 120 | NCH₃ | 4-NO₂—C₆H₄ | CO₂Me | Cl | H | —CH₂CH₂CH₂— |
| 121 | NCH₃ | 4-CF₃—C₆H₄ | CO₂Me | Cl | H | —CH₂CH₂CH₂— |
| 122 | NCH₃ | 4-CN—C₆H₄ | CO₂Me | Cl | H | —CH₂CH₂CH₂— |
| 123 | NCH₃ | 4-CH₃CO₂—C₆H₄ | CO₂Me | Cl | H | —CH₂CH₂CH₂— |
| 124 | NCH₃ | 4-CH₃S—C₆H₄ | CO₂Me | Cl | H | —CH₂CH₂CH₂— |
| 125 | NCH₃ | 4-CF₃O—C₆H₄ | CO₂Me | Cl | H | —CH₂CH₂CH₂— |
| 126 | NCH₃ | 2,4-2Cl—C₆H₃ | CO₂Me | Cl | H | —CH₂CH₂CH₂— |
| 127 | NCH(CH₃)₂ | 4-Cl—C₆H₄ | CO₂Me | Cl | H | —CH₂CH₂CH₂— |
| 128 | NCH₃ | 4-CH₃O—C₆H₄ | CO₂Me | Cl | H | —CH₂CH₂CH₂— |
| 129 | NC₂H₅ | C₆H₅ | H | Cl | H | —CH₂CH₂CH₂— |
| 130 | NC₂H₅ | 4-Cl—C₆H₄ | H | Cl | H | —CH₂CH₂CH₂— |
| 131 | NC₄H₉-n | C₆H₅ | H | Cl | H | —CH₂CH₂CH₂— |
| 132 | NC₄H₉-n | 4-Cl—C₆H₄ | H | Cl | H | —CH₂CH₂CH₂— |
| 133 | NC₂H₅ | C₆H₅ | CH₃ | Cl | H | —CH₂CH₂CH₂— |
| 134 | NC₂H₅ | 4-Cl—C₆H₄ | CH₃ | Cl | H | —CH₂CH₂CH₂— |
| 135 | NC₄H₉-n | C₆H₅ | CH₃ | Cl | H | —CH₂CH₂CH₂— |
| 136 | NC₄H₉-n | 4-Cl—C₆H₄ | CH₃ | Cl | H | —CH₂CH₂CH₂— |
| 137 | NCH₃ | C₆H₅ | H | H | H | —CH₂CH₂CH₂— |
| 138 | NCH₃ | 4-Cl—C₆H₄ | H | H | H | —CH₂CH₂CH₂— |
| 139 | NCH₃ | 4-F—C₆H₄ | H | H | H | —CH₂CH₂CH₂— |
| 140 | NCH₃ | 4-CF₃—C₆H₄ | H | H | H | —CH₂CH₂CH₂— |
| 141 | NCH₃ | 4-CH₃S—C₆H₄ | H | H | H | —CH₂CH₂CH₂— |
| 142 | NCH₃ | 2,4-2Cl—C₆H₃ | H | H | H | —CH₂CH₂CH₂— |
| 143 | NCH₃ | 4-CH₃O—C₆H₄ | H | H | H | —CH₂CH₂CH₂— |
| 144 | NCH₃ | 3-Cl—C₆H₄ | H | H | H | —CH₂CH₂CH₂— |
| 145 | NCH₃ | 4-Br—C₆H₄ | H | H | H | —CH₂CH₂CH₂— |
| 146 | NCH₃ | 2-Cl—C₆H₄ | H | H | H | —CH₂CH₂CH₂— |
| 147 | NCH₃ | C₆H₅ | H | Cl | Cl | —CH₂CH₂CH₂— |
| 148 | NCH₃ | 4-Cl—C₆H₄ | H | Cl | Cl | —CH₂CH₂CH₂— |
| 149 | NCH₃ | 4-CF₃—C₆H₄ | H | Cl | Cl | —CH₂CH₂CH₂— |
| 150 | NCH₃ | 4-CH₃S—C₆H₄ | H | Cl | Cl | —CH₂CH₂CH₂— |
| 151 | NCH₃ | 2,4-2Cl—C₆H₃ | H | Cl | Cl | —CH₂CH₂CH₂— |
| 152 | NCH₃ | 4-CH₃O—C₆H₄ | H | Cl | Cl | —CH₂CH₂CH₂— |
| 153 | NCH₃ | 3-Cl—C₆H₄ | H | Cl | Cl | —CH₂CH₂CH₂— |
| 154 | NCH₃ | 4-Br—C₆H₄ | H | Cl | Cl | —CH₂CH₂CH₂— |
| 155 | NCH₃ | 2-Cl—C₆H₄ | H | Cl | Cl | —CH₂CH₂CH₂— |
| 156 | NCH₃ | C₆H₅ | CH₃ | H | H | —CH₂CH₂CH₂— |
| 157 | NCH₃ | 4-Cl—C₆H₄ | CH₃ | H | H | —CH₂CH₂CH₂— |
| 158 | NCH₃ | 4-F—C₆H₄ | CH₃ | H | H | —CH₂CH₂CH₂— |

TABLE 10-continued

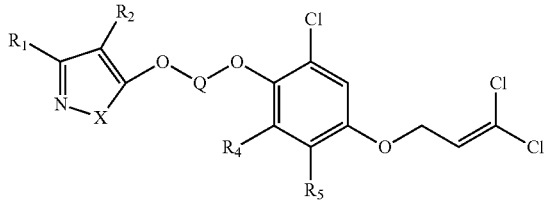

I-1

| No. | X | R₁ | R₂ | R₄ | R₅ | Q |
|---|---|---|---|---|---|---|
| 159 | NCH₃ | 4-CF₃—C₆H₄ | CH₃ | H | H | —CH₂CH₂CH₂— |
| 160 | NCH₃ | 4-CH₃S—C₆H₄ | CH₃ | H | H | —CH₂CH₂CH₂— |
| 161 | NCH₃ | 2,4-2Cl—C₆H₃ | CH₃ | H | H | —CH₂CH₂CH₂— |
| 162 | NCH₃ | 4-CH₃O—C₆H₄ | CH₃ | H | H | —CH₂CH₂CH₂— |
| 163 | NCH₃ | 3-Cl—C₆H₄ | CH₃ | H | H | —CH₂CH₂CH₂— |
| 164 | NCH₃ | 4-Br—C₆H₄ | CH₃ | H | H | —CH₂CH₂CH₂— |
| 165 | NCH₃ | 2-Cl—C₆H₄ | CH₃ | H | H | —CH₂CH₂CH₂— |
| 166 | NCH₃ | C₆H₅ | CH₃ | Cl | Cl | —CH₂CH₂CH₂— |
| 167 | NCH₃ | 4-Cl—C₆H₄ | CH₃ | Cl | Cl | —CH₂CH₂CH₂— |
| 168 | NCH₃ | 4-CF₃—C₆H₄ | CH₃ | Cl | Cl | —CH₂CH₂CH₂— |
| 169 | NCH₃ | 4-CH₃S—C₆H₄ | CH₃ | Cl | Cl | —CH₂CH₂CH₂— |
| 170 | NCH₃ | 2,4-2Cl—C₆H₃ | CH₃ | Cl | Cl | —CH₂CH₂CH₂— |
| 171 | NCH₃ | 4-CH₃O—C₆H₄ | CH₃ | Cl | Cl | —CH₂CH₂CH₂— |
| 172 | NCH₃ | 3-Cl—C₆H₄ | CH₃ | Cl | Cl | —CH₂CH₂CH₂— |
| 173 | NCH₃ | 4-Br—C₆H₄ | CH₃ | Cl | Cl | —CH₂CH₂CH₂— |
| 174 | NCH₃ | 2-Cl—C₆H₄ | CH₃ | Cl | Cl | —CH₂CH₂CH₂— |
| 175 | O | C₆H₅ | H | Cl | H | —CH₂CH₂CH₂— |
| 176 | O | 4-Cl—C₆H₄ | H | Cl | H | —CH₂CH₂CH₂— |
| 177 | O | 4-F—C₆H₄ | H | Cl | H | —CH₂CH₂CH₂— |
| 178 | O | 4-NO₂—C₆H₄ | H | Cl | H | —CH₂CH₂CH₂— |
| 179 | O | 4-CF₃—C₆H₄ | H | Cl | H | —CH₂CH₂CH₂— |
| 180 | O | 4-CN—C₆H₄ | H | Cl | H | —CH₂CH₂CH₂— |
| 181 | O | 4-CH₃CO₂—C₆H₄ | H | Cl | H | —CH₂CH₂CH₂— |
| 182 | O | 4-CH₃S—C₆H₄ | H | Cl | H | —CH₂CH₂CH₂— |
| 183 | O | 4-CH₃SO₂—C₆H₄ | H | Cl | H | —CH₂CH₂CH₂— |
| 184 | O | 4-CF₃O—C₆H₄ | H | Cl | H | —CH₂CH₂CH₂— |
| 185 | O | 2,4-2Cl—C₆H₃ | H | Cl | H | —CH₂CH₂CH₂— |
| 186 | O | 4-CH₃O—C₆H₄ | H | Cl | H | —CH₂CH₂CH₂— |
| 187 | O | 2-Cl-4-F—C₆H₃ | H | Cl | H | —CH₂CH₂CH₂— |
| 188 | O | 3-Cl—C₆H₄ | H | Cl | H | —CH₂CH₂CH₂— |
| 189 | O | 4-Br—C₆H₄ | H | Cl | H | —CH₂CH₂CH₂— |
| 190 | O | C₆H₅ | Cl | Cl | H | —CH₂CH₂CH₂— |
| 191 | O | 4-Cl—C₆H₄ | Cl | Cl | H | —CH₂CH₂CH₂— |
| 192 | O | 4-F—C₆H₄ | Cl | Cl | H | —CH₂CH₂CH₂— |
| 193 | O | 4-NO₂—C₆H₄ | Cl | Cl | H | —CH₂CH₂CH₂— |
| 194 | O | 4-CF₃—C₆H₄ | Cl | Cl | H | —CH₂CH₂CH₂— |
| 195 | O | 4-CN—C₆H₄ | Cl | Cl | H | —CH₂CH₂CH₂— |
| 196 | O | 4-CH₃CO₂—C₆H₄ | Cl | Cl | H | —CH₂CH₂CH₂— |
| 197 | O | 4-CH₃S—C₆H₄ | Cl | Cl | H | —CH₂CH₂CH₂— |
| 198 | O | 4-CH₃SO₂—C₆H₄ | Cl | Cl | H | —CH₂CH₂CH₂— |
| 199 | O | 4-CF₃O—C₆H₄ | Cl | Cl | H | —CH₂CH₂CH₂— |
| 200 | O | 2,4-2Cl—C₆H₃ | Cl | Cl | H | —CH₂CH₂CH₂— |
| 201 | O | 4-CH₃O—C₆H₄ | Cl | Cl | H | —CH₂CH₂CH₂— |
| 202 | O | 2-Cl-4-F—C₆H₃ | Cl | Cl | H | —CH₂CH₂CH₂— |
| 203 | O | 3-Cl—C₆H₄ | Cl | Cl | H | —CH₂CH₂CH₂— |
| 204 | O | 4-Br—C₆H₄ | Cl | Cl | H | —CH₂CH₂CH₂— |
| 205 | O | C₆H₅ | CH₃ | Cl | H | —CH₂CH₂CH₂— |
| 206 | O | 4-Cl—C₆H₄ | CH₃ | Cl | H | —CH₂CH₂CH₂— |
| 207 | O | 4-F—C₆H₄ | CH₃ | Cl | H | —CH₂CH₂CH₂— |
| 208 | O | 4-NO₂—C₆H₄ | CH₃ | Cl | H | —CH₂CH₂CH₂— |
| 209 | O | 4-CF₃—C₆H₄ | CH₃ | Cl | H | —CH₂CH₂CH₂— |
| 210 | O | 4-CN—C₆H₄ | CH₃ | Cl | H | —CH₂CH₂CH₂— |
| 211 | O | 4-CH₃CO₂—C₆H₄ | CH₃ | Cl | H | —CH₂CH₂CH₂— |
| 212 | O | 4-CH₃S—C₆H₄ | CH₃ | Cl | H | —CH₂CH₂CH₂— |
| 213 | O | 4-CH₃SO₂—C₆H₄ | CH₃ | Cl | H | —CH₂CH₂CH₂— |
| 214 | O | 4-CF₃O—C₆H₄ | CH₃ | Cl | H | —CH₂CH₂CH₂— |
| 215 | O | 2,4-2Cl—C₆H₃ | CH₃ | Cl | H | —CH₂CH₂CH₂— |
| 216 | O | 4-CH₃O—C₆H₄ | CH₃ | Cl | H | —CH₂CH₂CH₂— |
| 217 | O | 3-Cl—C₆H₄ | CH₃ | Cl | H | —CH₂CH₂CH₂— |
| 218 | O | 4-Br—C₆H₄ | CH₃ | Cl | H | —CH₂CH₂CH₂— |
| 219 | O | 4-CH₃—C₆H₄ | CH₃ | Cl | H | —CH₂CH₂CH₂— |
| 220 | NPh | CF₃ | H | Cl | H | —CH₂CH₂CH₂— |
| 221 | N(Ph-4-Cl) | C₆H₅ | H | Cl | H | —CH₂CH₂CH₂— |
| 222 | NCH₃ | CF₃ | Ph | Cl | H | —CH₂CH₂CH₂— |
| 223 | NCH₃ | C₆H₅ | Ph | Cl | H | —CH₂CH₂CH₂— |
| 224 | NCH₃ | C₆H₅ | H | Cl | H | —CH₂CH₂— |

TABLE 10-continued

I-1

| No. | X | R₁ | R₂ | R₄ | R₅ | Q |
|---|---|---|---|---|---|---|
| 225 | NCH₃ | 4-Cl—C₆H₄ | H | Cl | H | —CH₂CH₂— |
| 226 | NCH₃ | 4-F—C₆H₄ | H | Cl | H | —CH₂CH₂— |
| 227 | NCH₃ | 4-NO₂—C₆H₄ | H | Cl | H | —CH₂CH₂— |
| 228 | NCH₃ | 4-CF₃—C₆H₄ | H | Cl | H | —CH₂CH₂— |
| 229 | NCH₃ | 4-CN—C₆H₄ | H | Cl | H | —CH₂CH₂— |
| 230 | NCH₃ | 4-CH₃—C₆H₄ | H | Cl | H | —CH₂CH₂— |
| 231 | NCH₃ | 4-CH₃O—C₆H₄ | H | Cl | H | —CH₂CH₂— |
| 232 | NCH₃ | 4-CH₃CH₂—C₆H₄ | H | Cl | H | —CH₂CH₂— |
| 233 | NCH₃ | 4-CF₃O—C₆H₄ | H | Cl | H | —CH₂CH₂— |
| 234 | NCH₃ | 2,4-2Cl—C₆H₃ | H | Cl | H | —CH₂CH₂— |
| 235 | NCH₃ | C₆H₅ | CH₃ | Cl | H | —CH₂CH₂— |
| 236 | NCH₃ | 4-Cl—C₆H₄ | CH₃ | Cl | H | —CH₂CH₂— |
| 237 | NCH₃ | 4-F—C₆H₄ | CH₃ | Cl | H | —CH₂CH₂— |
| 238 | NCH₃ | 4-NO₂—C₆H₄ | CH₃ | Cl | H | —CH₂CH₂— |
| 239 | NCH₃ | 4-CF₃—C₆H₄ | CH₃ | Cl | H | —CH₂CH₂— |
| 240 | NCH₃ | 4-CN—C₆H₄ | CH₃ | Cl | H | —CH₂CH₂— |
| 241 | NCH₃ | 4-CH₃—C₆H₄ | CH₃ | Cl | H | —CH₂CH₂— |
| 242 | NCH₃ | 4-CH₃S—C₆H₄ | CH₃ | Cl | H | —CH₂CH₂— |
| 243 | NCH₃ | 4-CH₃CH₂—C₆H₄ | CH₃ | Cl | H | —CH₂CH₂— |
| 244 | NCH₃ | 4-CF₃O—C₆H₄ | CH₃ | Cl | H | —CH₂CH₂— |
| 245 | NCH₃ | 2,4-2Cl—C₆H₃ | CH₃ | Cl | H | —CH₂CH₂— |
| 246 | NCH₃ | C₆H₅ | H | Cl | H | —CH₂CH₂CH₂CH₂— |
| 247 | NCH₃ | 4-Cl—C₆H₄ | H | Cl | H | —CH₂CH₂CH₂CH₂— |
| 248 | NCH₃ | 4-Cl—C₆H₄ | H | H | H | —CH₂CH₂CH₂CH₂— |
| 249 | NCH₃ | C₆H₅ | H | H | H | —CH₂CH₂CH₂CH₂— |
| 250 | NCH₃ | C₆H₅ | H | Cl | Cl | —CH₂CH₂CH₂CH₂— |
| 251 | NCH₃ | 4-Cl—C₆H₄ | H | Cl | Cl | —CH₂CH₂CH₂CH₂— |
| 252 | NCH₃ | 4-CF₃—C₆H₄ | H | Cl | H | —CH₂CH₂CH₂CH₂— |
| 253 | NCH₃ | 4-CH₃—C₆H₄ | H | Cl | H | —CH₂CH₂CH₂CH₂— |
| 254 | NCH₃ | 4-CH₃O—C₆H₄ | H | Cl | H | —CH₂CH₂CH₂CH₂— |
| 255 | NCH₃ | 4-CH₃CH₂—C₆H₄ | H | Cl | H | —CH₂CH₂CH₂CH₂— |
| 256 | NCH₃ | 2,4-2Cl—C₆H₃ | H | Cl | H | —CH₂CH₂CH₂CH₂— |
| 257 | NCH₃ | C₆H₅ | CH₃ | Cl | H | —CH₂CH₂CH₂CH₂— |
| 258 | NCH₃ | 4-Cl—C₆H₄ | CH₃ | Cl | H | —CH₂CH₂CH₂CH₂— |
| 259 | NCH₃ | 4-F—C₆H₄ | CH₃ | Cl | H | —CH₂CH₂CH₂CH₂— |
| 260 | NCH₃ | 4-NO₂—C₆H₄ | CH₃ | Cl | H | —CH₂CH₂CH₂CH₂— |
| 261 | NCH₃ | 4-CF₃—C₆H₄ | CH₃ | Cl | H | —CH₂CH₂CH₂CH₂— |
| 262 | NCH₃ | 4-CN—C₆H₄ | CH₃ | Cl | H | —CH₂CH₂CH₂CH₂— |
| 263 | NCH₃ | 4-CH₃—C₆H₄ | CH₃ | Cl | H | —CH₂CH₂CH₂CH₂— |
| 264 | NCH₃ | 4-CH₃S—C₆H₄ | CH₃ | Cl | H | —CH₂CH₂CH₂CH₂— |
| 265 | NCH₃ | 4-CH₃CH₂—C₆H₄ | CH₃ | Cl | H | —CH₂CH₂CH₂CH₂— |
| 266 | NCH₃ | 4-CF₃O—C₆H₄ | CH₃ | Cl | H | —CH₂CH₂CH₂CH₂— |
| 267 | NCH₃ | 2,4-2Cl—C₆H₃ | CH₃ | Cl | H | —CH₂CH₂CH₂CH₂— |

TABLE 11

I-2

| No. | X | R₁ | R₂ | R₄ | R₅ | Q |
|---|---|---|---|---|---|---|
| 268 | NCH₃ | C₆H₅ | H | Cl | H | —CH₂CH₂CH₂— |
| 269 | NCH₃ | 4-Cl—C₆H₄ | H | Cl | H | —CH₂CH₂CH₂— |
| 270 | NCH₃ | 4-F—C₆H₄ | H | Cl | H | —CH₂CH₂CH₂— |
| 271 | NCH₃ | 4-NO₂—C₆H₄ | H | Cl | H | —CH₂CH₂CH₂— |

TABLE 11-continued

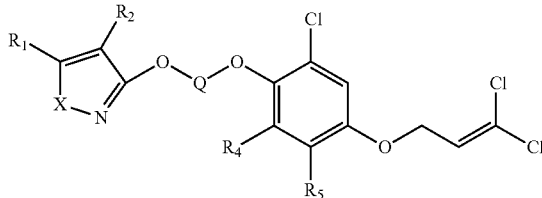

I-2

| No. | X | R₁ | R₂ | R₄ | R₅ | Q |
|---|---|---|---|---|---|---|
| 272 | NCH₃ | 4-CF₃—C₆H₄ | H | Cl | H | —CH₂CH₂CH₂— |
| 273 | NCH₃ | 4-CN—C₆H₄ | H | Cl | H | —CH₂CH₂CH₂— |
| 274 | NCH₃ | 4-CH₃CO₂—C₆H₄ | H | Cl | H | —CH₂CH₂CH₂— |
| 275 | NCH₃ | 4-CH₃S—C₆H₄ | H | Cl | H | —CH₂CH₂CH₂— |
| 276 | NCH₃ | 4-CH₃SO₂—C₆H₄ | H | Cl | H | —CH₂CH₂CH₂— |
| 277 | NCH₃ | 4-CF₃O—C₆H₄ | H | Cl | H | —CH₂CH₂CH₂— |
| 278 | NCH₃ | 2,4-2Cl—C₆H₃ | H | Cl | H | —CH₂CH₂CH₂— |
| 279 | NCH(CH₃)₂ | 4-Cl—C₆H₄ | H | Cl | H | —CH₂CH₂CH₂— |
| 280 | NCH₃ | 4-CH₃O—C₆H₄ | H | Cl | H | —CH₂CH₂CH₂— |
| 281 | NCH₃ | 2-Cl-4-F—C₆H₃ | H | Cl | H | —CH₂CH₂CH₂— |
| 282 | NCH₃ | 3-Cl—C₆H₄ | H | Cl | H | —CH₂CH₂CH₂— |
| 283 | NCH₃ | 4-Br—C₆H₄ | H | Cl | H | —CH₂CH₂CH₂— |
| 284 | NCH₃ | 4-CH₃—C₆H₄ | H | Cl | H | —CH₂CH₂CH₂— |
| 285 | NCH₃ | 4-C₂H₅—C₆H₄ | H | Cl | H | —CH₂CH₂CH₂— |
| 286 | NCH₃ | 4-CF₃CH₂O—C₆H₄ | H | Cl | H | —CH₂CH₂CH₂— |
| 287 | NCH₃ | 4-PhO—C₆H₄ | H | Cl | H | —CH₂CH₂CH₂— |
| 288 | NCH₃ | 2-Cl—C₆H₄ | H | Cl | H | —CH₂CH₂CH₂— |
| 289 | NCH₃ | 3,4-2CH₃O—C₆H₃ | H | Cl | H | —CH₂CH₂CH₂— |
| 290 | NCH₃ | 3,5-2Cl—C₆H₃ | H | Cl | H | —CH₂CH₂CH₂— |
| 291 | NCH₃ | 2-CH₃O—C₆H₄ | H | Cl | H | —CH₂CH₂CH₂— |
| 292 | NCH₃ | 2,5-2CH₃-Thiophen-3-yl | H | Cl | H | —CH₂CH₂CH₂— |
| 293 | NCH₃ | 2,4-2CH₃—C₆H₃ | H | Cl | H | —CH₂CH₂CH₂— |
| 294 | NCH₃ | 3,4-2CH₃—C₆H₃ | H | Cl | H | —CH₂CH₂CH₂— |
| 295 | NCH₃ | 2,5-2CH₃—C₆H₃ | H | Cl | H | —CH₂CH₂CH₂— |
| 296 | NCH₃ | 2,6-2CH₃—C₆H₃ | H | Cl | H | —CH₂CH₂CH₂— |
| 297 | NCH₃ | 6-CH₃O-Pyridin-3-yl | H | Cl | H | —CH₂CH₂CH₂— |
| 298 | NCH₃ | 6-CF₃CH₂O-Pyridin-3-yl | H | Cl | H | —CH₂CH₂CH₂— |
| 299 | NCH₃ | 4-(4-Cl—Ph)—C₆H₄ | H | Cl | H | —CH₂CH₂CH₂— |
| 300 | NCH₃ | Thiophen-2-yl | H | Cl | H | —CH₂CH₂CH₂— |
| 301 | NCH₃ | 5-Cl-Thiophen-2-yl | H | Cl | H | —CH₂CH₂CH₂— |
| 302 | NCH₃ | Thiazol-2-yl | H | Cl | H | —CH₂CH₂CH₂— |
| 303 | NCH₃ | Furan-2-yl | H | Cl | H | —CH₂CH₂CH₂— |
| 304 | NCH₃ | 4-i-C₃H₇—C₆H₄ | H | Cl | H | —CH₂CH₂CH₂— |
| 305 | NCH₃ | 4-n-C₃H₇—C₆H₄ | H | Cl | H | —CH₂CH₂CH₂— |
| 306 | NCH₃ | 4-t-C₄H₉—C₆H₄ | H | Cl | H | —CH₂CH₂CH₂— |
| 307 | NCH₃ | 2,4,6-3CH₃—C₆H₂ | H | Cl | H | —CH₂CH₂CH₂— |
| 308 | NCH₃ | 2,4,6-3Cl—C₆H₂ | H | Cl | H | —CH₂CH₂CH₂— |
| 309 | NCH₃ | C₆H₅ | Cl | Cl | H | —CH₂CH₂CH₂— |
| 310 | NCH₃ | 4-Cl—C₆H₄ | Cl | Cl | H | —CH₂CH₂CH₂— |
| 311 | NCH₃ | 4-F—C₆H₄ | Cl | Cl | H | —CH₂CH₂CH₂— |
| 312 | NCH₃ | 4-NO₂—C₆H₄ | Cl | Cl | H | —CH₂CH₂CH₂— |
| 313 | NCH₃ | 4-CF₃—C₆H₄ | Cl | Cl | H | —CH₂CH₂CH₂— |
| 314 | NCH₃ | 4-CN—C₆H₄ | Cl | Cl | H | —CH₂CH₂CH₂— |
| 315 | NCH₃ | 4-CH₃CO₂—C₆H₄ | Cl | Cl | H | —CH₂CH₂CH₂— |
| 316 | NCH₃ | 4-CH₃S—C₆H₄ | Cl | Cl | H | —CH₂CH₂CH₂— |
| 317 | NCH₃ | 4-CH₃SO₂—C₆H₄ | Cl | Cl | H | —CH₂CH₂CH₂— |
| 318 | NCH₃ | 4-CF₃O—C₆H₄ | Cl | Cl | H | —CH₂CH₂CH₂— |
| 319 | NCH₃ | 2,4-2Cl—C₆H₃ | Cl | Cl | H | —CH₂CH₂CH₂— |
| 320 | NCH(CH₃)₂ | 4-Cl—C₆H₄ | Cl | Cl | H | —CH₂CH₂CH₂— |
| 321 | NCH₃ | 4-CH₃O—C₆H₄ | Cl | Cl | H | —CH₂CH₂CH₂— |
| 322 | NCH₃ | 2-Cl-4-F—C₆H₃ | Cl | Cl | H | —CH₂CH₂CH₂— |
| 323 | NCH₃ | 3-Cl—C₆H₄ | Cl | Cl | H | —CH₂CH₂CH₂— |
| 324 | NCH₃ | 4-Br—C₆H₄ | Cl | Cl | H | —CH₂CH₂CH₂— |
| 325 | NCH₃ | 4-CH₃—C₆H₄ | Cl | Cl | H | —CH₂CH₂CH₂— |
| 326 | NCH₃ | 4-C₂H₅—C₆H₄ | Cl | Cl | H | —CH₂CH₂CH₂— |
| 327 | NCH₃ | 4-CF₃CH₂O—C₆H₄ | Cl | Cl | H | —CH₂CH₂CH₂— |
| 328 | NCH₃ | 4-PhO—C₆H₄ | Cl | Cl | H | —CH₂CH₂CH₂— |
| 329 | NCH₃ | 2-Cl—C₆H₄ | Cl | Cl | H | —CH₂CH₂CH₂— |
| 330 | NCH₃ | 3,4-2CH₃O—C₆H₃ | Cl | Cl | H | —CH₂CH₂CH₂— |
| 331 | NCH₃ | 3,5-2Cl—C₆H₃ | Cl | Cl | H | —CH₂CH₂CH₂— |
| 332 | NCH₃ | 2-CH₃O—C₆H₄ | Cl | Cl | H | —CH₂CH₂CH₂— |
| 333 | NCH₃ | 2,5-2CH₃-Thiophen-3-yl | Cl | Cl | H | —CH₂CH₂CH₂— |
| 334 | NCH₃ | 2,4-2CH₃—C₆H₃ | Cl | Cl | H | —CH₂CH₂CH₂— |
| 335 | NCH₃ | 3,4-2CH₃—C₆H₃ | Cl | Cl | H | —CH₂CH₂CH₂— |
| 336 | NCH₃ | 2,5-2CH₃—C₆H₃ | Cl | Cl | H | —CH₂CH₂CH₂— |
| 337 | NCH₃ | 2,6-2CH₃—C₆H₃ | Cl | Cl | H | —CH₂CH₂CH₂— |

TABLE 11-continued

I-2

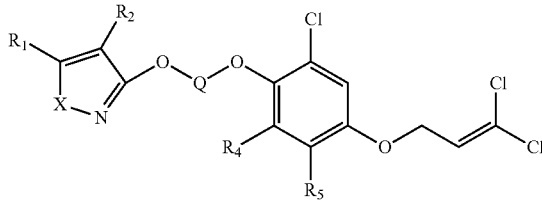

| No. | X | R₁ | R₂ | R₄ | R₅ | Q |
|---|---|---|---|---|---|---|
| 338 | NCH₃ | 6-CH₃O-Pyridin-3-yl | Cl | Cl | H | —CH₂CH₂CH₂— |
| 339 | NCH₃ | 6-CF₃CH₂O-Pyridin-3-yl | Cl | Cl | H | —CH₂CH₂CH₂— |
| 340 | NCH₃ | 4-(4-Cl—Ph)—C₆H₄ | Cl | Cl | H | —CH₂CH₂CH₂— |
| 341 | NCH₃ | Thiophen-2-yl | Cl | Cl | H | —CH₂CH₂CH₂— |
| 342 | NCH₃ | 5-Cl-Thiophen-2-yl | Cl | Cl | H | —CH₂CH₂CH₂— |
| 343 | NCH₃ | Thiazol-2-yl | Cl | Cl | H | —CH₂CH₂CH₂— |
| 344 | NCH₃ | Furan-2-yl | Cl | Cl | H | —CH₂CH₂CH₂— |
| 345 | NCH₃ | 4-i-C₃H₇—C₆H₄ | Cl | Cl | H | —CH₂CH₂CH₂— |
| 346 | NCH₃ | 4-n-C₃H₇—C₆H₄ | Cl | Cl | H | —CH₂CH₂CH₂— |
| 347 | NCH₃ | 4-t-C₄H₉—C₆H₄ | Cl | Cl | H | —CH₂CH₂CH₂— |
| 348 | NCH₃ | 2,4,6-3CH₃—C₆H₂ | Cl | Cl | H | —CH₂CH₂CH₂— |
| 349 | NCH₃ | 2,4,6-3Cl—C₆H₂ | Cl | Cl | H | —CH₂CH₂CH₂— |
| 350 | NCH₃ | C₆H₅ | CH₃ | Cl | H | —CH₂CH₂CH₂— |
| 351 | NCH₃ | 4-Cl—C₆H₄ | CH₃ | Cl | H | —CH₂CH₂CH₂— |
| 352 | NCH₃ | 4-F—C₆H₄ | CH₃ | Cl | H | —CH₂CH₂CH₂— |
| 353 | NCH₃ | 4-NO₂—C₆H₄ | CH₃ | Cl | H | —CH₂CH₂CH₂— |
| 354 | NCH₃ | 4-CF₃—C₆H₄ | CH₃ | Cl | H | —CH₂CH₂CH₂— |
| 355 | NCH₃ | 4-CN—C₆H₄ | CH₃ | Cl | H | —CH₂CH₂CH₂— |
| 356 | NCH₃ | 4-CH₃CH₂O—C₆H₄ | CH₃ | Cl | H | —CH₂CH₂CH₂— |
| 357 | NCH₃ | 4-CH₃S—C₆H₄ | CH₃ | Cl | H | —CH₂CH₂CH₂— |
| 358 | NCH₃ | 4-CH₃SO₂—C₆H₄ | CH₃ | Cl | H | —CH₂CH₂CH₂— |
| 359 | NCH₃ | 4-CF₃O—C₆H₄ | CH₃ | Cl | H | —CH₂CH₂CH₂— |
| 360 | NCH₃ | 2,4-2Cl—C₆H₃ | CH₃ | Cl | H | —CH₂CH₂CH₂— |
| 361 | NCH₃ | 3,4-2Cl—C₆H₃ | CH₃ | Cl | H | —CH₂CH₂CH₂— |
| 362 | NCH(CH₃)₂ | 4-Cl—C₆H₄ | CH₃ | Cl | H | —CH₂CH₂CH₂— |
| 363 | NCH₃ | 4-CH₃O—C₆H₄ | CH₃ | Cl | H | —CH₂CH₂CH₂— |
| 364 | NCH₃ | 2-Cl-4-F—C₆H₃ | CH₃ | Cl | H | —CH₂CH₂CH₂— |
| 365 | NCH₃ | 3-Cl—C₆H₄ | CH₃ | Cl | H | —CH₂CH₂CH₂— |
| 366 | NCH₃ | 4-Br—C₆H₄ | CH₃ | Cl | H | —CH₂CH₂CH₂— |
| 367 | NCH₃ | 4-CH₃—C₆H₄ | CH₃ | Cl | H | —CH₂CH₂CH₂— |
| 368 | NCH₃ | 4-C₂H₅—C₆H₄ | CH₃ | Cl | H | —CH₂CH₂CH₂— |
| 369 | NCH₃ | 4-CF₃CH₂O—C₆H₄ | CH₃ | Cl | H | —CH₂CH₂CH₂— |
| 370 | NCH₃ | 4-PhO—C₆H₄ | CH₃ | Cl | H | —CH₂CH₂CH₂— |
| 371 | NCH₃ | 2-Cl—C₆H₄ | CH₃ | Cl | H | —CH₂CH₂CH₂— |
| 372 | NCH₃ | 3,4-2CH₃O—C₆H₃ | CH₃ | Cl | H | —CH₂CH₂CH₂— |
| 373 | NCH₃ | 3,5-2Cl—C₆H₃ | CH₃ | Cl | H | —CH₂CH₂CH₂— |
| 374 | NCH₃ | 2-CH₃O—C₆H₄ | CH₃ | Cl | H | —CH₂CH₂CH₂— |
| 375 | NCH₃ | 2,5-2CH₃-Thiophen-3-yl | CH₃ | Cl | H | —CH₂CH₂CH₂— |
| 376 | NCH₃ | 2,4-2CH₃—C₆H₃ | CH₃ | Cl | H | —CH₂CH₂CH₂— |
| 377 | NCH₃ | 3,4-2CH₃—C₆H₃ | CH₃ | Cl | H | —CH₂CH₂CH₂— |
| 378 | NCH₃ | 2,5-2CH₃—C₆H₃ | CH₃ | Cl | H | —CH₂CH₂CH₂— |
| 379 | NCH₃ | 2,6-2CH₃—C₆H₃ | CH₃ | Cl | H | —CH₂CH₂CH₂— |
| 380 | NCH₃ | 6-CH₃O-Pyridin-3-yl | CH₃ | Cl | H | —CH₂CH₂CH₂— |
| 381 | NCH₃ | 6-CF₃CH₂O-Pyridin-3-yl | CH₃ | Cl | H | —CH₂CH₂CH₂— |
| 382 | NCH₃ | 4-(4-Cl—Ph)—C₆H₄ | CH₃ | Cl | H | —CH₂CH₂CH₂— |
| 383 | NCH₃ | Thiophen-2-yl | CH₃ | Cl | H | —CH₂CH₂CH₂— |
| 384 | NCH₃ | 5-Cl-Thiophen-2-yl | CH₃ | Cl | H | —CH₂CH₂CH₂— |
| 385 | NCH₃ | Thiazol-2-yl | CH₃ | Cl | H | —CH₂CH₂CH₂— |
| 386 | NCH₃ | Furan-2-yl | CH₃ | Cl | H | —CH₂CH₂CH₂— |
| 387 | NCH₃ | 4-i-C₃H₇—C₆H₄ | CH₃ | Cl | H | —CH₂CH₂CH₂— |
| 388 | NCH₃ | 4-n-C₃H₇—C₆H₄ | CH₃ | Cl | H | —CH₂CH₂CH₂— |
| 389 | NCH₃ | 4-t-C₄H₉—C₆H₄ | CH₃ | Cl | H | —CH₂CH₂CH₂— |
| 390 | NCH₃ | 2,4,6-3CH₃—C₆H₂ | CH₃ | Cl | H | —CH₂CH₂CH₂— |
| 391 | NCH₃ | 2,4,6-3Cl—C₆H₂ | CH₃ | Cl | H | —CH₂CH₂CH₂— |
| 392 | NCH₃ | C₆H₅ | CO₂Me | Cl | H | —CH₂CH₂CH₂— |
| 393 | NCH₃ | 4-Cl—C₆H₄ | CO₂Me | Cl | H | —CH₂CH₂CH₂— |
| 394 | NCH₃ | 4-F—C₆H₄ | CO₂Me | Cl | H | —CH₂CH₂CH₂— |
| 395 | NCH₃ | 4-NO₂—C₆H₄ | CO₂Me | Cl | H | —CH₂CH₂CH₂— |
| 396 | NCH₃ | 4-CF₃—C₆H₄ | CO₂Me | Cl | H | —CH₂CH₂CH₂— |
| 397 | NCH₃ | 4-CN—C₆H₄ | CO₂Me | Cl | H | —CH₂CH₂CH₂— |
| 398 | NCH₃ | 4-CH₃S—C₆H₄ | CO₂Me | Cl | H | —CH₂CH₂CH₂— |
| 399 | NCH₃ | 4-CH₃SO₂—C₆H₄ | CO₂Me | Cl | H | —CH₂CH₂CH₂— |
| 400 | NCH₃ | 4-CF₃O—C₆H₄ | CO₂Me | Cl | H | —CH₂CH₂CH₂— |
| 401 | NCH₃ | 2,4-2Cl—C₆H₃ | CO₂Me | Cl | H | —CH₂CH₂CH₂— |
| 402 | NCH(CH₃)₂ | 4-Cl—C₆H₄ | CO₂Me | Cl | H | —CH₂CH₂CH₂— |
| 403 | NCH₃ | 4-CH₃O—C₆H₄ | CO₂Me | Cl | H | —CH₂CH₂CH₂— |

TABLE 11-continued

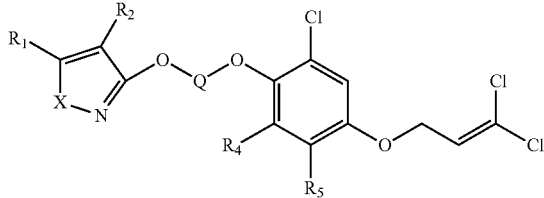

I-2

| No. | X | R$_1$ | R$_2$ | R$_4$ | R$_5$ | Q |
|---|---|---|---|---|---|---|
| 404 | NC$_2$H$_5$ | C$_6$H$_5$ | H | Cl | H | —CH$_2$CH$_2$CH$_2$— |
| 405 | NC$_2$H$_5$ | 4-Cl—C$_6$H$_4$ | H | Cl | H | —CH$_2$CH$_2$CH$_2$— |
| 406 | NC$_4$H$_9$-n | C$_6$H$_5$ | H | Cl | H | —CH$_2$CH$_2$CH$_2$— |
| 407 | NC$_4$H$_9$-n | 4-Cl—C$_6$H$_4$ | H | Cl | H | —CH$_2$CH$_2$CH$_2$— |
| 408 | NC$_2$H$_5$ | C$_6$H$_5$ | CH$_3$ | Cl | H | —CH$_2$CH$_2$CH$_2$— |
| 409 | NC$_2$H$_5$ | 4-Cl—C$_6$H$_4$ | CH$_3$ | Cl | H | —CH$_2$CH$_2$CH$_2$— |
| 410 | NC$_4$H$_9$-n | C$_6$H$_5$ | CH$_3$ | Cl | H | —CH$_2$CH$_2$CH$_2$— |
| 411 | NC$_4$H$_9$-n | 4-Cl—C$_6$H$_4$ | CH$_3$ | Cl | H | —CH$_2$CH$_2$CH$_2$— |
| 412 | NCH$_3$ | C$_6$H$_5$ | H | H | H | —CH$_2$CH$_2$CH$_2$— |
| 413 | NCH$_3$ | 4-Cl—C$_6$H$_4$ | H | H | H | —CH$_2$CH$_2$CH$_2$— |
| 414 | NCH$_3$ | 4-F—C$_6$H$_4$ | H | H | H | —CH$_2$CH$_2$CH$_2$— |
| 415 | NCH$_3$ | 4-CF$_3$—C$_6$H$_4$ | H | H | H | —CH$_2$CH$_2$CH$_2$— |
| 416 | NCH$_3$ | 4-CH$_3$S—C$_6$H$_4$ | H | H | H | —CH$_2$CH$_2$CH$_2$— |
| 417 | NCH$_3$ | 2,4-2Cl—C$_6$H$_3$ | H | H | H | —CH$_2$CH$_2$CH$_2$— |
| 418 | NCH$_3$ | 4-CH$_3$O—C$_6$H$_4$ | H | H | H | —CH$_2$CH$_2$CH$_2$— |
| 419 | NCH$_3$ | 3-Cl—C$_6$H$_4$ | H | H | H | —CH$_2$CH$_2$CH$_2$— |
| 420 | NCH$_3$ | 4-Br—C$_6$H$_4$ | H | H | H | —CH$_2$CH$_2$CH$_2$— |
| 421 | NCH$_3$ | 2-Cl—C$_6$H$_4$ | H | H | H | —CH$_2$CH$_2$CH$_2$— |
| 422 | NCH$_3$ | C$_6$H$_5$ | H | Cl | Cl | —CH$_2$CH$_2$CH$_2$— |
| 423 | NCH$_3$ | 4-Cl—C$_6$H$_4$ | H | Cl | Cl | —CH$_2$CH$_2$CH$_2$— |
| 424 | NCH$_3$ | 4-CF$_3$—C$_6$H$_4$ | H | Cl | Cl | —CH$_2$CH$_2$CH$_2$— |
| 425 | NCH$_3$ | 4-CH$_3$S—C$_6$H$_4$ | H | Cl | Cl | —CH$_2$CH$_2$CH$_2$— |
| 426 | NCH$_3$ | 2,4-2Cl—C$_6$H$_3$ | H | Cl | Cl | —CH$_2$CH$_2$CH$_2$— |
| 427 | NCH$_3$ | 4-CH$_3$O—C$_6$H$_4$ | H | Cl | Cl | —CH$_2$CH$_2$CH$_2$— |
| 428 | NCH$_3$ | 3-Cl—C$_6$H$_4$ | H | Cl | Cl | —CH$_2$CH$_2$CH$_2$— |
| 429 | NCH$_3$ | 4-Br—C$_6$H$_4$ | H | Cl | Cl | —CH$_2$CH$_2$CH$_2$— |
| 430 | NCH$_3$ | 2-Cl—C$_6$H$_4$ | H | Cl | Cl | —CH$_2$CH$_2$CH$_2$— |
| 431 | NCH$_3$ | C$_6$H$_5$ | CH$_3$ | H | H | —CH$_2$CH$_2$CH$_2$— |
| 432 | NCH$_3$ | 4-Cl—C$_6$H$_4$ | CH$_3$ | H | H | —CH$_2$CH$_2$CH$_2$— |
| 433 | NCH$_3$ | 4-F—C$_6$H$_4$ | CH$_3$ | H | H | —CH$_2$CH$_2$CH$_2$— |
| 434 | NCH$_3$ | 4-CF$_3$—C$_6$H$_4$ | CH$_3$ | H | H | —CH$_2$CH$_2$CH$_2$— |
| 435 | NCH$_3$ | 4-CH$_3$S—C$_6$H$_4$ | CH$_3$ | H | H | —CH$_2$CH$_2$CH$_2$— |
| 436 | NCH$_3$ | 2,4-2Cl—C$_6$H$_3$ | CH$_3$ | H | H | —CH$_2$CH$_2$CH$_2$— |
| 437 | NCH$_3$ | 4-CH$_3$O—C$_6$H$_4$ | CH$_3$ | H | H | —CH$_2$CH$_2$CH$_2$— |
| 438 | NCH$_3$ | 3-Cl—C$_6$H$_4$ | CH$_3$ | H | H | —CH$_2$CH$_2$CH$_2$— |
| 439 | NCH$_3$ | 4-Br—C$_6$H$_4$ | CH$_3$ | H | H | —CH$_2$CH$_2$CH$_2$— |
| 440 | NCH$_3$ | 2-Cl—C$_6$H$_4$ | CH$_3$ | H | H | —CH$_2$CH$_2$CH$_2$— |
| 441 | NCH$_3$ | C$_6$H$_5$ | CH$_3$ | Cl | Cl | —CH$_2$CH$_2$CH$_2$— |
| 442 | NCH$_3$ | 4-Cl—C$_6$H$_4$ | CH$_3$ | Cl | Cl | —CH$_2$CH$_2$CH$_2$— |
| 443 | NCH$_3$ | 4-CH$_3$—C$_6$H$_4$ | CH$_3$ | Cl | Cl | —CH$_2$CH$_2$CH$_2$— |
| 444 | NCH$_3$ | 4-C$_2$H$_5$—C$_6$H$_4$ | CH$_3$ | Cl | Cl | —CH$_2$CH$_2$CH$_2$— |
| 445 | NCH$_3$ | 2,4-2Cl—C$_6$H$_3$ | CH$_3$ | Cl | Cl | —CH$_2$CH$_2$CH$_2$— |
| 446 | NCH$_3$ | 4-CH$_3$O—C$_6$H$_4$ | CH$_3$ | Cl | Cl | —CH$_2$CH$_2$CH$_2$— |
| 447 | NCH$_3$ | 3-Cl—C$_6$H$_4$ | CH$_3$ | Cl | Cl | —CH$_2$CH$_2$CH$_2$— |
| 448 | NCH$_3$ | 4-Br—C$_6$H$_4$ | CH$_3$ | Cl | Cl | —CH$_2$CH$_2$CH$_2$— |
| 449 | NCH$_3$ | 2-Cl—C$_6$H$_4$ | CH$_3$ | Cl | Cl | —CH$_2$CH$_2$CH$_2$— |
| 450 | O | C$_6$H$_5$ | H | Cl | H | —CH$_2$CH$_2$CH$_2$— |
| 451 | O | 4-Cl—C$_6$H$_4$ | H | Cl | H | —CH$_2$CH$_2$CH$_2$— |
| 452 | O | 4-F—C$_6$H$_4$ | H | Cl | H | —CH$_2$CH$_2$CH$_2$— |
| 453 | O | 4-NO$_2$—C$_6$H$_4$ | H | Cl | H | —CH$_2$CH$_2$CH$_2$— |
| 454 | O | 4-CF$_3$—C$_6$H$_4$ | H | Cl | H | —CH$_2$CH$_2$CH$_2$— |
| 455 | O | 4-CN—C$_6$H$_4$ | H | Cl | H | —CH$_2$CH$_2$CH$_2$— |
| 456 | O | 4-CH$_3$CO$_2$—C$_6$H$_4$ | H | Cl | H | —CH$_2$CH$_2$CH$_2$— |
| 457 | O | 4-CH$_3$S—C$_6$H$_4$ | H | Cl | H | —CH$_2$CH$_2$CH$_2$— |
| 458 | O | 4-CH$_3$SO$_2$—C$_6$H$_4$ | H | Cl | H | —CH$_2$CH$_2$CH$_2$— |
| 459 | O | 4-CF$_3$O—C$_6$H$_4$ | H | Cl | H | —CH$_2$CH$_2$CH$_2$— |
| 460 | O | 2,4-2Cl—C$_6$H$_3$ | H | Cl | H | —CH$_2$CH$_2$CH$_2$— |
| 461 | O | 4-CH$_3$O—C$_6$H$_4$ | H | Cl | H | —CH$_2$CH$_2$CH$_2$— |
| 462 | O | 2-Cl-4-F—C$_6$H$_3$ | H | Cl | H | —CH$_2$CH$_2$CH$_2$— |
| 463 | O | 3-Cl—C$_6$H$_4$ | H | Cl | H | —CH$_2$CH$_2$CH$_2$— |
| 464 | O | 4-Br—C$_6$H$_4$ | H | Cl | H | —CH$_2$CH$_2$CH$_2$— |
| 465 | O | C$_6$H$_5$ | Cl | Cl | H | —CH$_2$CH$_2$CH$_2$— |
| 466 | O | 4-Cl—C$_6$H$_4$ | Cl | Cl | H | —CH$_2$CH$_2$CH$_2$— |
| 467 | O | 4-F—C$_6$H$_4$ | Cl | Cl | H | —CH$_2$CH$_2$CH$_2$— |
| 468 | O | 4-NO$_2$—C$_6$H$_4$ | Cl | Cl | H | —CH$_2$CH$_2$CH$_2$— |
| 469 | O | 4-CF$_3$—C$_6$H$_4$ | Cl | Cl | H | —CH$_2$CH$_2$CH$_2$— |

TABLE 11-continued

I-2

| No. | X | R₁ | R₂ | R₄ | R₅ | Q |
|---|---|---|---|---|---|---|
| 470 | O | 4-CN—C₆H₄ | Cl | Cl | H | —CH₂CH₂CH₂— |
| 471 | O | 4-CH₃CO₂—C₆H₄ | Cl | Cl | H | —CH₂CH₂CH₂— |
| 472 | O | 4-CH₃S—C₆H₄ | Cl | Cl | H | —CH₂CH₂CH₂— |
| 473 | O | 4-CH₃SO₂—C₆H₄ | Cl | Cl | H | —CH₂CH₂CH₂— |
| 474 | O | 4-CF₃O—C₆H₄ | Cl | Cl | H | —CH₂CH₂CH₂— |
| 475 | O | 2,4-2Cl—C₆H₃ | Cl | Cl | H | —CH₂CH₂CH₂— |
| 476 | O | 4-CH₃O—C₆H₄ | Cl | Cl | H | —CH₂CH₂CH₂— |
| 477 | O | 2-Cl-4-F—C₆H₃ | Cl | Cl | H | —CH₂CH₂CH₂— |
| 478 | O | 3-Cl—C₆H₄ | Cl | Cl | H | —CH₂CH₂CH₂— |
| 479 | O | 4-Br—C₆H₄ | Cl | Cl | H | —CH₂CH₂CH₂— |
| 480 | O | C₆H₅ | CH₃ | Cl | H | —CH₂CH₂CH₂— |
| 481 | O | 4-Cl—C₆H₄ | CH₃ | Cl | H | —CH₂CH₂CH₂— |
| 482 | O | 4-F—C₆H₄ | CH₃ | Cl | H | —CH₂CH₂CH₂— |
| 483 | O | 4-NO₂—C₆H₄ | CH₃ | Cl | H | —CH₂CH₂CH₂— |
| 484 | O | 4-CF₃—C₆H₄ | CH₃ | Cl | H | —CH₂CH₂CH₂— |
| 485 | O | 4-CN—C₆H₄ | CH₃ | Cl | H | —CH₂CH₂CH₂— |
| 486 | O | 4-CH₃CO₂—C₆H₄ | CH₃ | Cl | H | —CH₂CH₂CH₂— |
| 487 | O | 4-CH₃S—C₆H₄ | CH₃ | Cl | H | —CH₂CH₂CH₂— |
| 488 | O | 4-CH₃SO₂—C₆H₄ | CH₃ | Cl | H | —CH₂CH₂CH₂— |
| 489 | O | 4-CF₃O—C₆H₄ | CH₃ | Cl | H | —CH₂CH₂CH₂— |
| 490 | O | 2,4-2Cl—C₆H₃ | CH₃ | Cl | H | —CH₂CH₂CH₂— |
| 491 | O | 4-CH₃O—C₆H₄ | CH₃ | Cl | H | —CH₂CH₂CH₂— |
| 492 | O | 3-Cl—C₆H₄ | CH₃ | Cl | H | —CH₂CH₂CH₂— |
| 493 | O | 4-Br—C₆H₄ | CH₃ | Cl | H | —CH₂CH₂CH₂— |
| 494 | O | 4-CH₃—C₆H₄ | CH₃ | Cl | H | —CH₂CH₂CH₂— |
| 495 | NPh | CF₃ | H | Cl | H | —CH₂CH₂CH₂— |
| 496 | N(Ph-4-Cl) | C₆H₅ | H | Cl | H | —CH₂CH₂CH₂— |
| 497 | NCH₃ | CF₃ | Ph | Cl | H | —CH₂CH₂CH₂— |
| 498 | NCH₃ | C₆H₅ | Ph | Cl | H | —CH₂CH₂CH₂— |
| 499 | NCH₃ | C₆H₅ | H | Cl | H | —CH₂CH₂— |
| 500 | NCH₃ | 4-Cl—C₆H₄ | H | Cl | H | —CH₂CH₂— |
| 501 | NCH₃ | 4-F—C₆H₄ | H | Cl | H | —CH₂CH₂— |
| 502 | NCH₃ | 4-NO₂—C₆H₄ | H | Cl | H | —CH₂CH₂— |
| 503 | NCH₃ | 4-CF₃—C₆H₄ | H | Cl | H | —CH₂CH₂— |
| 504 | NCH₃ | 4-CN—C₆H₄ | H | Cl | H | —CH₂CH₂— |
| 505 | NCH₃ | 4-CH₃—C₆H₄ | H | Cl | H | —CH₂CH₂— |
| 506 | NCH₃ | 4-CH₃O—C₆H₄ | H | Cl | H | —CH₂CH₂— |
| 507 | NCH₃ | 4-CH₃CH₂—C₆H₄ | H | Cl | H | —CH₂CH₂— |
| 508 | NCH₃ | 4-CF₃O—C₆H₄ | H | Cl | H | —CH₂CH₂— |
| 509 | NCH₃ | 2,4-2Cl—C₆H₃ | H | Cl | H | —CH₂CH₂— |
| 510 | NCH₃ | C₆H₅ | CH₃ | Cl | H | —CH₂CH₂— |
| 511 | NCH₃ | 4-Cl—C₆H₄ | CH₃ | Cl | H | —CH₂CH₂— |
| 512 | NCH₃ | 4-F—C₆H₄ | CH₃ | Cl | H | —CH₂CH₂— |
| 513 | NCH₃ | 4-NO₂—C₆H₄ | CH₃ | Cl | H | —CH₂CH₂— |
| 514 | NCH₃ | 4-CF₃—C₆H₄ | CH₃ | Cl | H | —CH₂CH₂— |
| 515 | NCH₃ | 4-CN—C₆H₄ | CH₃ | Cl | H | —CH₂CH₂— |
| 516 | NCH₃ | 4-CH₃—C₆H₄ | CH₃ | Cl | H | —CH₂CH₂— |
| 517 | NCH₃ | 4-CH₃S—C₆H₄ | CH₃ | Cl | H | —CH₂CH₂— |
| 518 | NCH₃ | 4-CH₃CH₂—C₆H₄ | CH₃ | Cl | H | —CH₂CH₂— |
| 519 | NCH₃ | 4-CF₃O—C₆H₄ | CH₃ | Cl | H | —CH₂CH₂— |
| 520 | NCH₃ | 2,4-2Cl—C₆H₃ | CH₃ | Cl | H | —CH₂CH₂— |
| 521 | NCH₃ | C₆H₅ | H | Cl | H | —CH₂CH₂CH₂CH₂— |
| 522 | NCH₃ | 4-Cl—C₆H₄ | H | Cl | H | —CH₂CH₂CH₂CH₂— |
| 523 | NCH₃ | 4-F—C₆H₄ | H | Cl | H | —CH₂CH₂CH₂CH₂— |
| 524 | NCH₃ | 4-NO₂—C₆H₄ | H | Cl | H | —CH₂CH₂CH₂CH₂— |
| 525 | NCH₃ | 4-CF₃—C₆H₄ | H | Cl | H | —CH₂CH₂CH₂CH₂— |
| 526 | NCH₃ | 4-CN—C₆H₄ | H | Cl | H | —CH₂CH₂CH₂CH₂— |
| 527 | NCH₃ | 4-CH₃—C₆H₄ | H | Cl | H | —CH₂CH₂CH₂CH₂— |
| 528 | NCH₃ | 4-CH₃O—C₆H₄ | H | Cl | H | —CH₂CH₂CH₂CH₂— |
| 529 | NCH₃ | 4-CH₃CH₂—C₆H₄ | H | Cl | H | —CH₂CH₂CH₂CH₂— |
| 530 | NCH₃ | 4-CF₃O—C₆H₄ | H | Cl | H | —CH₂CH₂CH₂CH₂— |
| 531 | NCH₃ | 2,4-2Cl—C₆H₃ | H | Cl | H | —CH₂CH₂CH₂CH₂— |
| 532 | NCH₃ | C₆H₅ | CH₃ | Cl | H | —CH₂CH₂CH₂CH₂— |
| 533 | NCH₃ | 4-Cl—C₆H₄ | CH₃ | Cl | H | —CH₂CH₂CH₂CH₂— |
| 534 | NCH₃ | 4-F—C₆H₄ | CH₃ | Cl | H | —CH₂CH₂CH₂CH₂— |
| 535 | NCH₃ | 4-NO₂—C₆H₄ | CH₃ | Cl | H | —CH₂CH₂CH₂CH₂— |

TABLE 11-continued

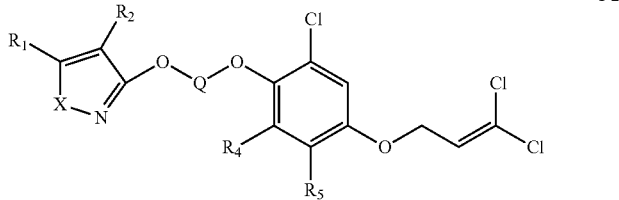

I-2

| No. | X | R$_1$ | R$_2$ | R$_4$ | R$_5$ | Q |
|---|---|---|---|---|---|---|
| 536 | NCH$_3$ | 4-CF$_3$—C$_6$H$_4$ | CH$_3$ | Cl | H | —CH$_2$CH$_2$CH$_2$CH$_2$— |
| 537 | NCH$_3$ | 4-CN—C$_6$H$_4$ | CH$_3$ | Cl | H | —CH$_2$CH$_2$CH$_2$CH$_2$— |
| 538 | NCH$_3$ | 4-CH$_3$—C$_6$H$_4$ | CH$_3$ | Cl | H | —CH$_2$CH$_2$CH$_2$CH$_2$— |
| 539 | NCH$_3$ | 4-CH$_3$S—C$_6$H$_4$ | CH$_3$ | Cl | H | —CH$_2$CH$_2$CH$_2$CH$_2$— |
| 540 | NCH$_3$ | 4-CH$_3$CH$_2$—C$_6$H$_4$ | CH$_3$ | Cl | H | —CH$_2$CH$_2$CH$_2$CH$_2$— |
| 541 | NCH$_3$ | 4-CF$_3$O—C$_6$H$_4$ | CH$_3$ | Cl | H | —CH$_2$CH$_2$CH$_2$CH$_2$— |
| 542 | NCH$_3$ | 2,4-2Cl—C$_6$H$_3$ | CH$_3$ | Cl | H | —CH$_2$CH$_2$CH$_2$CH$_2$— |

TABLE 12

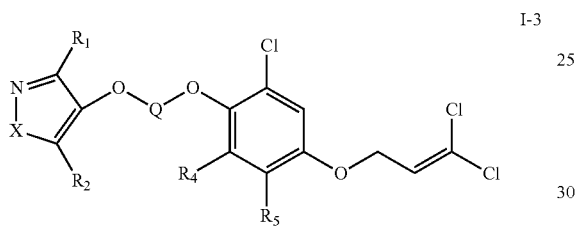

I-3

| No. | X | R$_1$ | R$_2$ | R$_4$ | R$_5$ | Q |
|---|---|---|---|---|---|---|
| 543 | NPh | CF$_3$ | H | Cl | H | —CH$_2$CH$_2$CH$_2$— |
| 544 | N(Ph-4-Cl) | CH$_3$ | H | Cl | H | —CH$_2$CH$_2$CH$_2$— |
| 545 | NPh | H | H | Cl | H | —CH$_2$CH$_2$CH$_2$— |
| 546 | N(Ph-4-Cl) | H | H | Cl | H | —CH$_2$CH$_2$CH$_2$— |
| 547 | N(Ph-4-CF$_3$) | H | H | Cl | H | —CH$_2$CH$_2$CH$_2$— |
| 548 | N(Ph-2-CH$_3$-4-Cl) | H | H | Cl | H | —CH$_2$CH$_2$CH$_2$— |
| 549 | NPh | CO$_2$C$_2$H$_5$ | H | Cl | H | —CH$_2$CH$_2$CH$_2$— |
| 550 | N(Ph-4-Cl) | CO$_2$C$_2$H$_5$ | H | Cl | H | —CH$_2$CH$_2$CH$_2$— |
| 551 | N(Ph-2-CH$_3$-4-Cl) | CO$_2$C$_2$H$_5$ | H | Cl | H | —CH$_2$CH$_2$CH$_2$— |
| 552 | N(Ph-2-CH$_3$) | H | H | Cl | H | —CH$_2$CH$_2$CH$_2$— |
| 553 | N(Ph-2-CH$_3$) | CO$_2$C$_2$H$_5$ | H | Cl | H | —CH$_2$CH$_2$CH$_2$— |
| 554 | N(Ph-4-CH$_3$) | H | H | Cl | H | —CH$_2$CH$_2$CH$_2$— |
| 555 | N(Ph-2-Cl) | H | H | Cl | H | —CH$_2$CH$_2$CH$_2$— |
| 556 | N(Ph-4-OCH$_3$) | H | H | Cl | H | —CH$_2$CH$_2$CH$_2$— |
| 557 | N(Ph-2,4-2Cl) | H | H | Cl | H | —CH$_2$CH$_2$CH$_2$— |
| 558 | N(Ph-4-F) | H | H | Cl | H | —CH$_2$CH$_2$CH$_2$— |
| 559 | NCH$_3$ | C$_6$H$_5$ | H | Cl | H | —CH$_2$CH$_2$CH$_2$— |
| 560 | NCH$_3$ | 4-Cl—C$_6$H$_4$ | H | Cl | H | —CH$_2$CH$_2$CH$_2$— |
| 561 | NCH$_3$ | 4-F—C$_6$H$_4$ | H | Cl | H | —CH$_2$CH$_2$CH$_2$— |
| 562 | NCH$_3$ | 4-CH$_3$—C$_6$H$_4$ | H | Cl | H | —CH$_2$CH$_2$CH$_2$— |
| 563 | NCH$_3$ | 4-CF$_3$—C$_6$H$_4$ | H | Cl | H | —CH$_2$CH$_2$CH$_2$— |
| 564 | NCH$_3$ | 2,4-2Cl—C$_6$H$_3$ | H | Cl | H | —CH$_2$CH$_2$CH$_2$— |

The compounds represented by the general formula (I) were prepared by condensation reaction of intermediate pyrazole or isoxazole compounds containing hydroxy group represented by the general formula (II) with haloallyl intermediates represented by the general formula (IV) under basic conditions, or by condensation reaction of intermediate pyrazole or isoxazole compounds represented by the general formula (III) with haloallyl intermediates containing hydroxy group represented by the general formula (V) under basic conditions according to the following schemes:

-continued

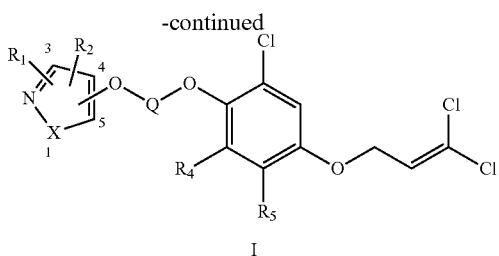

The compounds of the general formula (III) and (IV), wherein L is leaving group, selected from Cl or Br, other groups are as defined above.

The compounds of the general formula (IV) and (V) can be prepared according to the known methods, which disclosed in the patents including CN1860874, US20030073847 and WO9727173, etc.

The reaction was carried out in proper solvent and the proper solvent mentioned may be selected from tetrahydrofuran, acetonitrile, toluene, xylene, benzene, DMF, DMSO, acetone or butanone and so on.

The proper base mentioned may be selected from potassium hydroxide, sodium hydroxide, sodium carbonate, potassium carbonate, sodium bicarbonate, triethylamine, pyridine, sodium methoxide, sodium ethoxide, sodium hydride, potassium tert-butoxide or sodium tert-butoxide and so on.

The proper temperature mentioned is from room temperature to boiling point of the solvent, normal temperature is from 20 to 100° C.

The reaction time is in the range of 30 minutes to 20 hours, generally being 1-10 hours.

Intermediate represented by the general formula (II) can be purchased or prepared according to the known methods. Wherein, when hydroxy group is at 3- or 5-position of 5-member heterocycle, intermediate represented by the general formula (II) can be prepared by reaction of intermediate represented by the general formula (VI) with (substituted) hydrazine or hydroxylamine, according to the methods disclosed in WO2005080344A1, Synlett 2004, 5, 795-798, J. Chem. Soc., Perkin Trans. 2, 1987, 969-975 and so on. When hydroxy group is at 4-position of 5-membered heterocycle, intermediate represented by the general formula (II) can be prepared by cyclization from amines and the intermediate obtained by esterification of intermediate represented by the general formula (VI), referring to Organic Preparation and Procedures International, 2002, 34(1): 98-102. Intermediate represented by the general formula (III) can be prepared by halogenation of intermediate represented by the general formula (II).

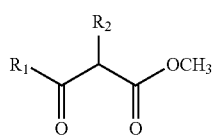

The compounds having general formula (I) have a high insecticidal activity against adults, larvae and eggs of insects which are harmful in the agricultural, civil and zoo-technical fields, the compounds also exhibit preferable fungicidal activity. A further object of the present invention therefore relates to the use of the compounds having general formula (I) as insecticides and/or fungicides, both in agriculture and other fields.

In particular, the compounds having general formula (I) are active against important species of lepidopteran such as striped rice borer (*Chilo suppressalis*), rice leaf roller (*Cnaphalocrocis medinalis*), corn borer (*Pyrausta nubilalis*), tobacco budworm (*Heliothis virescens*), fruit moth, diamond back moth (*Plutella xylostella*), beet armyworm (*Laphygma exigua*), cotton leafworm (*Spodoptera litura*) and so on, especially showed very good control of diamond back moth and beet armyworm at very low doses. The compounds in present invention also have high activity against *homoptera* such as aphids etc. Therefore the compounds of general formula (I) in the invention prefer to be used to control the pests of *lepidoptera* and *homoptera* in agriculture and other fields. Additionally, some compounds in present invention also exhibit good fungicidal activity, which can be used to control rice blast, tomato late blight, vegetable grey mould, wheat powdery mildew, cucumber downy mildew, anthracnose, etc, especially showed very good control of rice blast, cucumber downy mildew and anthracnose.

Meanwhile, the compounds having general formula (I) have a low toxicity to many useful insects and mites, mammals, fishes and birds, furthermore, the compounds have no phytotoxicity.

Thanks to their positive characteristics, the compounds in the invention can be advantageously used in protecting crops of farming and gardening, domestic and breeding animals, as well as environments frequented by human beings, from harmful insects and fungi.

In order to obtain the desired effect, the dosage of compound to be applied can vary with various factors, for example, the used compound, the protected crop, the type of harmful organism, the degree of infestation, the climatic conditions, the application method and the adopted formulation.

Doses of compound in the range of 10 g to 1000 g per hectare generally can provide a sufficient control to the harmful insects and fungi.

An another object of the present invention also relates to a method for controlling insects and/or phytopathogenic fungi in crops of farming and gardening and/or on domestic and breeding animals and/or environments frequented by human beings, by the application of the compounds having general formula (I). In particular, the dosage of compound to be applied varies from 10 g to 1000 g per hectare.

For practical use in agriculture, it is usually useful to use compositions containing one or more compounds having general formula (I).

Therefore a further object of the present invention relates to insecticidal and/or fungicidal compositions containing one or more compounds having general formula (I) as active ingredient, and the weight percentage of the active ingredient in the composition is 0.1-99%.

Compositions can be used in the form of dry powders, wettable powders, emulsifiable concentrates, microemulsions, pastes, granulates, solutions, suspensions, etc.: the selection of the type of composition depends on the specific use.

The compositions are prepared in the known way, for example by diluting or dissolving the active substance with a solvent medium and/or a solid diluent, optionally in the presence of surface-active agents.

Solid diluents or carriers which can be used include, for example: silica, kaolin, bentonite, talc, diatomite, dolomite, calcium carbonate, magnesia, chalk, clays, synthetic silicates, attapulgite, seppiolite and so on.

Liquid diluents which can be used include, for example, in addition to water, aromatic organic solvents (xylols or mixtures of alkylbenzols, chlorobenzene, etc.), paraffins (petroleum fractions), alcohols (methanol, propanol, butanol, octanol, glycerin), esters (ethyl acetate, isobutyl acetate, etc.), ketones (cyclohexanone, acetone, acetophenone, isophorone, ethylamylketone, etc.), amides (N,N-dimethylformamide, N-methylpyrrolidone, etc.).

Surface-active agents which can be used include salts of sodium, calcium, triethylamine or triethanolamine of alkylsulfonates, alkylarylsulfonates, polyethoxylated alkylphenols, polyethoxylated esters of sorbitol, ligninsulfonates, etc.

The compositions can also contain special additives for particular purposes, for example adhesion agents such Arabic gum, polyvinyl alcohol, polyvinyl-pyrrolidone, etc.

The concentration of active ingredient in the above compositions can vary within a wide range depending on the active compound, the applications for which they are destined, the environmental conditions and the type of adopted formulation. In general the concentration of active ingredient ranges from 0.5 to 90%, preferably from 5 to 60%.

If required, other active ingredients being compatible with the compounds having general formula (I) can be added to the compositions, such as, other acaricides/insecticides, fungicides, plant growth regulators, antibiotics, herbicides, fertilizers.

The preparation methods of several common formulations examples in the present invention are as follows:

The preparation of suspension concentrate: in commonly used for producing the suspension concentrate, the active component in formula is 5%-35%. With water as the medium, the compound in the invention, dispersing agent, suspending agent and antifreeze are added to sanding machine for grinding to make suspension concentrate.

The preparation of water emulsion: the compound in the invention, solvent and emulsifier are mixed together, to make a homogeneous oil phase. The water is mixed with antifreeze to make a homogeneous water phase. In the high-speed stirring, the aqueous phase is added to the oil phase or oil phase is added to the aqueous phase, forming the water emulsion with good dispersity. The active component of water emulsions is generally 5%-15% in this invention. For the production of concentrated emulsions, the compounds of this invention are dissolved in one or more of the mixed solvent, and then emulsifier was added to enhance dispersion effects in the water.

The preparation of wettable powder: according to formulation requirements, the compound in the invention, surfactants and solid diluents are mixed well, after smashing through ultrafine pulverizer, that is the wettable powder products (for example, 10%-60%). For the preparation of the spraying wettable powder, the compounds of this invention can be formed the mixture with solid powder, such as clay, inorganic silicates, carbonates, as well as wetting agents, adhesives and/or dispersant agent.

The preparation of water dispersible granules: the compound in the invention and powdered solid diluents, wetting agents and adhesives are mixed to smash, kneading together with water, added to the granulation certain mesh machine for granulation, then by drying and sieving (at the scope screen). Also, the compound, in the invention dispersants, disintegrants, wetting agents and solid diluent are added to sanding machine, grinding in water to produce suspension and then spray-drying granulation, usually the content of the prepared granular products is 20%-30%.

DESCRIPTION OF THE INVENTION IN DETAIL

The following examples are illustrative of the present invention, but without being restricted thereby.

Preparation Example

Example 1

The Preparation of Intermediate

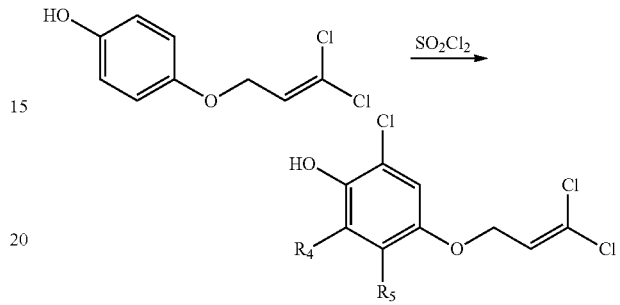

Sulfonyl chloride (0.95-3 equiv) in toluene was added dropwise to a solution of 4-(3,3-dichloroallyloxy)phenol (4.10 g, 18.5 mmol) and di-n-butylamine 4 drop (0.1 mL) in toluene (30 mL) at 65-70° C. for 2 h and the reaction mixture stirred at room temperature for further 1-2 h and monitored by TLC. After the reaction was over, the mixture was diluted with saturated sodium hydrogen carbonate solution, toluene layer was separated and water layer was extracted with toluene. The organic layer was combined, dried and evaporated. The residue was purified via silica gel column chromatography to obtain intermediate.

| $R_4$ | $R_5$ | Rate of charge 4-(3,3-dichloroallyloxy)phenol (I):$SO_2Cl_2$ | Reaction temperature (° C.) | Reaction time (h) | Yield (%) |
|---|---|---|---|---|---|
| H | H | 1:0.95-1 | 65-70 | 1 | 85 |
| Cl | H | 1:1.85-2 | 65-70 | 1 | 60-70 |
| Cl | Cl | 1:3 | 65-70 | 2 | 90 |

Example 2

The preparation of Intermediate IV-1

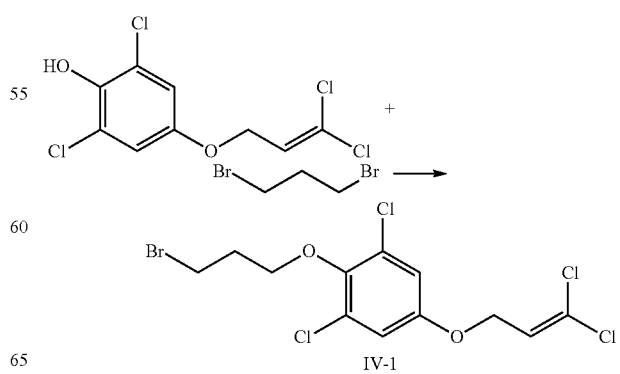

2,6-Dichloro-4-(3',3'-dichloroallyloxy)phenol (3.8 g) in 10 mL DMF was added dropwise to a solution of 1,3-dibromopropane (4.2 g) and anhydrous potassium carbonate (2.9 g) in 20 mL DMF at 15° C. for 1 h and the reaction was monitored by TLC. After the reaction was over, the mixture was diluted with 50 mL brine and extracted with ethyl acetate (60 mL) three times. The combined extracts were dried, evaporated and the residue was purified via silica gel column chromatography to obtain intermediate IV-1 (4.35 g).

Example 3

The Preparation of Compound 2

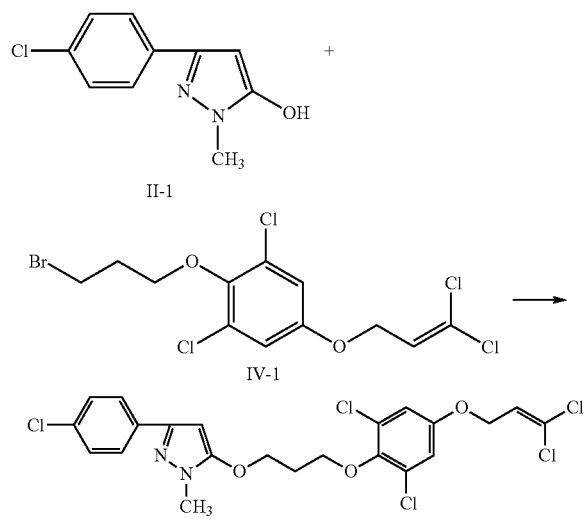

Intermediate II-1 (0.22 g, prepared according to the method disclosed in WO 2005080344A1) and anhydrous potassium carbonate (0.23 g) were added to a 100 mL flask, then 40 mL DMF and intermediate IV-1 (0.45 g) were added to the solution. The reaction mixture was heated to 35° C. for 3 h and monitored by TLC. After the reaction was over, the mixture was evaporated under reduced pressure, diluted with 50 mL brine and extracted with ethyl acetate (60 mL) for three times. The combined extracts were dried and evaporated and the crude product was purified via silica gel column chromatography to obtain compound 2 (0.37 g).

Example 4

The Preparation of Compound 269

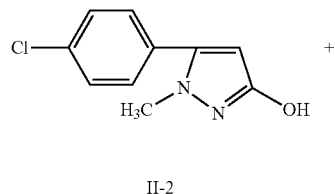

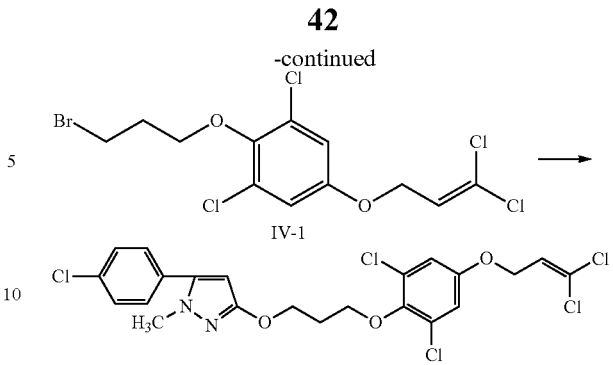

Intermediate II-2 (0.18 g, prepared according to the method disclosed by J. Chem. Soc., Perkin Trans. 2, 1987, 969-975) and anhydrous potassium carbonate (0.20 g) were added to a 100 mL flask, then 40 mL DMF and intermediate IV-1 (0.40 g) were added to the solution. The reaction mixture was heated to 35° C. for 3 h and monitored by TLC. After the reaction was over, the mixture was evaporated under reduced pressure, diluted with 50 mL brine and extracted with ethyl acetate (60 mL) for three times. The combined extracts were dried and evaporated and the crude product was purified via silica gel column chromatography to obtain compound 269 (0.33 g).

Example 5

The Preparation of Compound 367

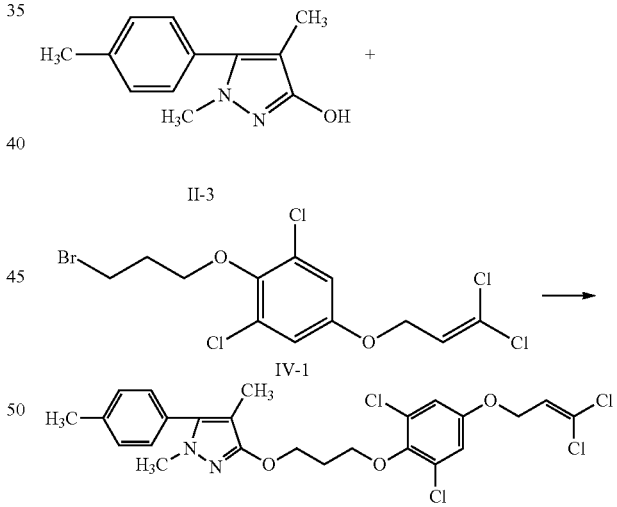

Intermediate II-3 (0.24 g, prepared according to the method disclosed by J. Chem. Soc., Perkin Trans. 2, 1987, 969-975) and anhydrous potassium carbonate (0.27 g) were added to a 100 mL flask, then 40 mL DMF and intermediate IV-1 (0.49 g) were added to the solution. The reaction mixture was heated to 35° C. for 3 h and monitored by TLC. After the reaction was over, the mixture was evaporated under reduced pressure, diluted with 50 mL brine and extracted with ethyl acetate (60 mL) for three times. The combined extracts were dried and evaporated and the crude product was purified via silica gel column chromatography to obtain compound 367 (0.30 g).

Example 6

The Preparation of Compound 546

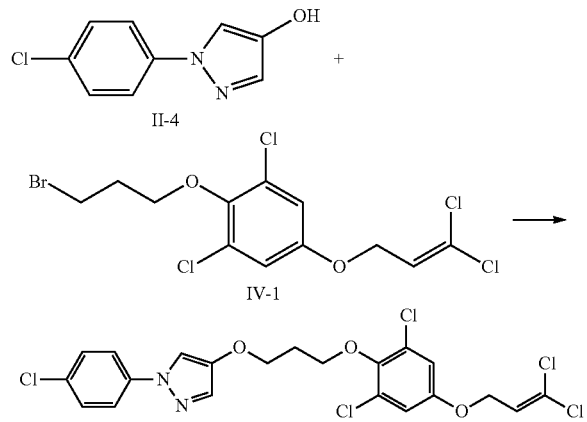

Intermediate II-4 (0.25 g, prepared according to the method disclosed in Organic Preparation and Procedures International, 2002, 34(1): 98-102) and anhydrous potassium carbonate (0.28 g) were added to a 100 mL flask, then 40 mL DMF and intermediate IV-1 (0.52 g) were added to the solution. The reaction mixture was heated to 35° C. for 3 h and monitored by TLC. After the reaction was over, the mixture was evaporated under reduced pressure, diluted with 50 mL brine and extracted with ethyl acetate (60 mL) for three times. The combined extracts were dried and evaporated and the crude product was purified via silica gel column chromatography to obtain compound 546 (0.35 g).

Other compounds of the general formula (I) were prepared according to the above examples.

Melting point and $^1$HNMR spectrum ($^1$HNMR, 300 MHz, internal standard: TMS, solvent CDCl$_3$) of some compounds of this invention are as follows:

Compound 1: oil. δppm 7.75 (m, 2H), 7.38 (m, 2H), 7.28 (m, 1H), 6.85 (s, 2H), 6.11 (t, 1H), 5.89 (s, 1H), 4.58 (d, 2H), 4.42 (t, 2H), 4.15 (t, 2H), 3.71 (s, 3H), 2.32 (m, 2H).

Compound 2: m.p. 68-70° C. δppm 7.68 (m, 2H), 7.33 (m, 2H), 6.85 (s, 2H), 6.11 (t, 1H), 5.85 (s, 1H), 4.58 (d, 2H), 4.41 (t, 2H), 4.15 (t, 2H), 3.70 (s, 3H), 2.32 (m, 2H).

Compound 8: oil. δppm 7.67 (m, 2H), 7.27 (m, 2H), 6.84 (s, 2H), 6.12 (t, 1H), 5.84 (s, 1H), 4.59 (d, 2H), 4.40 (t, 2H), 4.14 (t, 2H), 3.69 (s, 3H), 2.50 (s, 3H), 2.32 (m, 2H).

Compound 13: m.p. 78-80° C. δppm 7.67 (m, 2H), 6.91 (m, 4H), 6.11 (t, 1H), 5.81 (s, 1H), 4.58 (d, 2H), 4.40 (t, 2H), 4.15 (t, 2H), 3.83 (s, 3H), 3.69 (s, 3H), 2.32 (m, 2H).

Compound 16: oil. δppm 7.64 (m, 2H), 7.50 (m, 2H), 6.85 (s, 2H), 6.11 (t, 1H), 5.86 (s, 1H), 4.58 (d, 2H), 4.41 (t, 2H), 4.14 (t, 2H), 3.70 (s, 3H), 2.32 (m, 2H).

Compound 21: oil. δppm 7.78 (m, 1H), 7.42 (m, 1H), 7.23 (m, 2H), 6.84 (s, 2H), 6.11 (m, 2H), 4.58 (d, 2H), 4.42 (t, 2H), 4.16 (t, 2H), 3.72 (s, 3H), 2.33 (m, 2H).

Compound 76: oil. δppm 7.63 (d, 2H), 7.41 (t, 2H), 7.32 (t, 1H), 6.83 (s, 2H), 6.10 (t, 1H), 4.58 (d, 2H), 4.40 (t, 2H), 4.18 (t, 2H), 3.76 (s, 3H), 2.31 (m, 2H), 2.17 (s, 3H).

Compound 130: oil. δppm 7.70 (m, 2H), 7.34 (m, 2H), 6.84 (s, 2H), 6.12 (t, 1H), 4.58 (d, 2H), 4.42 (t, 2H), 4.15 (t, 2H), 4.04 (m, 2H), 2.32 (m, 2H), 1.37 (m, 3H).

Compound 148: oil. δppm 7.68 (d, 2H), 7.33 (d, 2H), 7.08 (s, 1H), 6.39 (t, 1H), 6.10 (t, 1H), 4.77 (d, 2H), 4.39 (t, 2H), 4.24 (t, 2H), 3.64 (s, 3H), 2.34 (m, 2H).

Compound 166: oil. δppm 7.55 (m, 2H), 7.35 (m, 2H), 7.25 (m, 1H), 7.02 (s, 1H), 6.35 (t, 1H), 4.76 (d, 2H), 4.35 (t, 2H), 4.18 (t, 2H), 3.69 (s, 3H), 2.30 (m, 2H), 2.14 (s, 3H).

Compound 225: m.p. 117-119° C. δppm 7.72 (d, 2H), 7.39 (d, 2H), 7.10 (s, 2H), 6.41 (t, 1H), 6.17 (s, 1H), 4.66 (d, 2H), 4.44 (t, 2H), 4.31 (t, 2H), 3.59 (s, 3H).

Compound 235: oil. δppm 7.58 (d, 2H), 7.39 (t, 2H), 7.28 (t, 1H), 7.11 (s, 2H), 6.38 (t, 1H), 4.66 (d, 2H), 4.44 (t, 2H), 4.23 (t, 2H), 3.71 (s, 3H), 2.14 (s, 3H).

Compound 247: oil. δppm 7.67 (d, 2H), 7.31 (d, 2H), 6.96 (s, 2H), 6.27 (t, 1H), 5.96 (s, 1H), 4.63 (d, 2H), 4.20 (t, 2H), 3.99 (t, 2H), 3.63 (s, 3H), 2.02 (m, 4H).

Compound 248: oil. δppm 7.68 (d, 2H), 7.45 (d, 2H), 7.33 (d, 2H), 7.01 (s, 1H), 6.33 (t, 1H), 5.71 (s, 1H), 4.64 (d, 2H), 3.97 (t, 2H), 3.68 (t, 2H), 3.56 (s, 3H), 1.94 (m, 4H).

Compound 257: oil. δppm 7.56 (d, 2H), 7.34 (t, 2H), 7.22 (t, 1H), 6.93 (s, 2H), 6.22 (t, 1H), 4.62 (d, 2H), 4.16 (t, 2H), 4.01 (t, 2H), 3.69 (s, 3H), 2.13 (s, 3H), 2.04 (s, 4H).

Compound 268: oil. δppm 7.43 (m, 5H), 6.84 (s, 2H), 6.15 (t, 1H), 5.68 (s, 1H), 4.60 (d, 2H), 4.43 (t, 2H), 4.18 (t, 2H), 3.77 (s, 3H), 2.32 (m, 2H).

Compound 269: m.p. 63-64° C. δ7.46 (d, 2H), 7.35 (d, 2H), 6.84 (s, 2H), 6.11 (t, 1H), 5.77 (s, 1H), 4.58 (d, 2H), 4.50 (t, 2H), 4.15 (t, 2H), 3.81 (s, 3H), 2.32 (m, 2H).

Compound 350: oil. δppm 7.49 (m, 3H), 7.45 (m, 2H), 6.96 (s, 1H), 6.92 (s, 1H), 4.48 (m, 2H), 4.17 (m, 2H), 3.64 (s, 3H), 2.31 (m, 2H), 1.88 (s, 3H), 1.25 (s, 3H).

Compound 352: oil. δppm 7.30 (m, 2H), 7.18 (m, 2H), 6.84 (s, 2H), 6.12 (t, 1H), 4.58 (d, 2H), 4.49 (t, 2H), 4.17 (t, 2H), 3.60 (s, 3H), 2.32 (m, 2H), 1.85 (s, 3H).

Compound 356: oil. δppm 7.22 (m, 2H), 6.98 (m, 2H), 6.84 (s, 2H), 6.11 (t, 1H), 4.58 (d, 2H), 4.46 (t, 2H), 4.17 (t, 2H), 4.06 (m, 2H), 3.42 (s, 3H), 2.32 (m, 2H), 1.86 (s, 3H), 1.45 (m, 3H).

Compound 360: oil. δppm 7.52 (m, 1H), 7.33 (m, 1H), 7.18 (m, 1H), 6.82 (s, 2H), 6.10 (t, 1H), 4.56 (d, 2H), 4.45 (t, 2H), 4.15 (t, 2H), 3.47 (s, 3H), 2.31 (m, 2H), 1.74 (s, 3H).

Compound 361: oil. δppm 7.55 (m, 1H), 7.41 (m, 1H), 7.16 (m, 1H), 6.84 (s, 2H), 6.11 (t, 1H), 4.58 (d, 2H), 4.49 (t, 2H), 4.17 (t, 2H), 3.62 (s, 3H), 2.32 (m, 2H), 1.86 (s, 3H).

Compound 363: oil. δppm 7.25 (m, 2H), 6.98 (m, 2H), 6.84 (s, 2H), 6.12 (t, 1H), 4.58 (d, 2H), 4.47 (t, 2H), 4.17 (t, 2H), 3.86 (s, 3H), 3.61 (s, 3H), 2.32 (m, 2H), 1.86 (s, 3H).

Compound 367: oil. δppm 7.28 (d, 2H), 7.21 (d, 2H), 6.84 (s, 2H), 6.12 (t, 1H), 4.60 (d, 2H), 4.47 (t, 2H), 4.17 (m, 2H), 3.61 (s, 3H), 2.42 (s, 3H), 2.32 (t, 2H), 1.86 (s, 3H).

Compound 368: oil. δppm 7.21-7.31 (m, 4H), 6.84 (s, 2H), 6.12 (t, 1H), 4.58 (d, 2H), 4.47 (t, 2H), 4.17 (t, 2H), 3.62 (s, 3H), 2.71 (m, 2H), 2.32 (m, 2H), 1.87 (s, 3H), 1.28 (t, 3H).

Compound 376: oil. δppm 7.12 (s, 1H), 7.06 (m, 2H), 6.84 (s, 2H), 6.12 (t, 1H), 4.57 (d, 2H), 4.47 (t, 2H), 4.19 (t, 2H), 3.43 (s, 3H), 2.38 (s, 3H), 2.30 (t, 2H), 2.10 (s, 3H), 1.73 (s, 3H).

Compound 377: oil. δppm 7.24 (m, 1H), 7.07 (m, 2H), 6.84 (s, 2H), 6.11 (t, 1H), 4.58 (d, 2H), 4.49 (t, 2H), 4.17 (t, 2H), 3.62 (s, 3H), 2.34 (s, 6H), 2.32 (m, 2H), 1.86 (s, 3H).

Compound 378: oil. δppm 7.17 (m, 2H), 6.96 (s, 1H), 6.84 (s, 2H), 6.10 (t, 1H), 4.57 (d, 2H), 4.48 (t, 2H), 4.18 (t, 2H), 3.43 (s, 3H), 2.34 (s, 3H), 2.32 (m, 2H), 2.08 (s, 3H), 1.73 (s, 3H).

Compound 387: oil. δppm 7.31 (d, 2H), 7.23 (d, 2H), 6.84 (s, 2H), 6.12 (t, 1H), 4.58 (d, 2H), 4.48 (t, 2H), 4.17 (t, 2H), 3.63 (s, 3H), 2.93 (m, 1H), 2.32 (m, 2H), 1.87 (s, 3H), 1.31 (s, 3H), 1.28 (s, 3H).

Compound 389: oil. δppm 7.46 (m, 2H), 7.25 (m, 2H), 6.84 (s, 2H), 6.12 (t, 1H), 4.58 (d, 2H), 4.46 (t, 2H), 4.18 (t, 2H), 3.62 (s, 3H), 2.31 (m, 2H), 1.88 (s, 3H), 1.36 (s, 9H).

Compound 423: oil. δppm 7.42 (d, 2H), 7.34 (d, 2H), 6.88 (s, 1H), 6.19 (t, 1H), 5.73 (s, 1H), 4.68 (d, 2H), 4.39 (t, 2H), 4.15 (t, 2H), 3.71 (s, 3H), 2.31 (m, 2H).

Compound 443: oil. δppm 7.30 (m, 3H), 7.21 (d, 2H), 6.31 (t, 1H), 4.76 (d, 2H), 4.35 (t, 2H), 4.11 (t, 2H), 3.55 (s, 3H), 2.40 (s, 3H), 1.80 (s, 3H).

Compound 444: oil. δppm 7.31 (d, 2H), 7.24 (d, 2H), 7.16 (s, 1H), 6.29 (t, 1H), 4.76 (d, 2H), 4.34 (t, 2H), 4.11 (t, 2H), 3.55 (s, 3H), 2.68 (m, 2H), 2.23 (q, 2H), 1.80 (s, 3H), 1.26 (t, 3 H).

Compound 499: oil. δ 7.44 (m, 3H), 7.32 (d, 2H), 6.96 (s, 2H), 6.27 (t, 1H), 4.63 (d, 2H), 4.45 (t, 2H), 4.28 (t, 2H), 3.57 (s, 3H), 1.82 (s, 3H).

Compound 500: m.p. 82-83° C. δppm 7.48 (s, 4H), 7.03 (s, 2H), 6.35 (t, 1H), 5.78 (s, 1H), 4.65 (d, 2H), 4.40 (t, 2H), 4.24 (t, 2H), 3.69 (s, 3H).

Compound 516: oil. δppm 7.27 (m, 2H), 7.18 (m, 2H), 6.85 (s, 2H), 6.12 (t, 1H), 4.59 (m, 4H), 4.36 (m, 2H), 3.60 (s, 3H), 2.41 (s, 3H), 1.87 (s, 3H).

Compound 518 (DMSO): oil. δppm 7.30 (m, 2H), 7.23 (m, 2H), 7.05 (s, 2H), 6.38 (m, 1H), 4.65 (m, 2H), 4.45 (m, 2H), 4.27 (m, 2H), 3.55 (s, 3H), 2.68 (m, 2H), 1.80 (s, 3H), 1.27 (m, 3H).

Compound 522: oil. δppm 7.43 (s, 4H), 6.94 (s, 2H), 6.24 (t, 1H), 5.65 (s, 1H), 4.63 (d, 2H), 4.17 (t, 2H), 3.98 (t, 2H), 3.69 (s, 3H), 1.96 (s, 4H).

Compound 532: oil. δppm 7.45 (m, 3H), 7.31 (d, 2H), 6.95 (s, 2H), 6.27 (t, 1H), 4.63 (d, 2H), 4.19 (t, 2H), 3.99 (t, 2H), 3.56 (s, 3H), 1.96 (s, 4H), 1.82 (s, 3H).

Compound 538 (DMSO): oil. δppm 7.26 (m, 2H), 7.19 (m, 2H), 7.03 (s, 2H), 6.36 (m, 1H), 4.64 (m, 2H), 4.17 (m, 2H), 3.98 (m, 2H), 3.53 (s, 3H), 2.38 (s, 3H), 1.94 (m, 4H), 1.79 (s, 3H).

Compound 540: oil. δppm 7.27 (m, 4H), 6.85 (s, 2H), 6.13 (t, 1H), 4.58 (m, 2H), 4.29 (m, 2H), 4.04 (m, 2H), 3.62 (s, 3H), 2.71 (m, 2H), 2.03 (m, 2H), 1.87 (s, 3H), 1.29 (t, 3H).

Compound 546: oil. δppm 7.58 (s, 1H), 7.56 (d, 2H), 7.50 (s, 1H), 7.38 (d, 2H), 6.84 (s, 2H), 6.10 (t, 1H), 4.59 (d, 2H), 4.24 (t, 2H), 4.14 (t, 2H), 2.27 (q, 2H).

Compound 547: oil. δppm 7.64 (d, 2H), 7.58 (s, 1H), 7.50 (s, 1H), 7.27 (d, 2H), 6.84 (s, 2H), 6.10 (t, 1H), 4.59 (d, 2H), 4.24 (t, 2H), 4.14 (t, 2H), 2.28 (q, 2H).

Compound 550: oil. δppm 7.76 (d, 2H), 7.65 (s, 1H), 7.29 (d, 2H), 6.38 (s, 2H), 6.10 (t, 1H), 4.56 (d, 2H), 4.44 (q, 2H), 4.33 (t, 2H), 4.19 (t, 2H), 2.35 (q, 2H), 1.41 (t, 3H).

Compound 551: oil. δppm 7.32 (s, 1H), 7.29 (d, 2H), 7.28 (s, 1H), 7.26 (d, 2H), 6.83 (s, 2H), 6.11 (t, 1H), 4.59 (d, 2H), 4.42 (q, 2H), 4.29 (t, 2H), 4.18 (t, 2H), 2.35 (q, 2H), 2.22 (s, 3H), 1.41 (t, 3H).

Formulation Example

Base on 100% Active Ingredient (Weight/Weight %))

Example 7

30% Wettable Powders

| Compound 2 | 30% |
| --- | --- |
| Sodium dodecyl sulfate | 2% |
| Lignin sulfonate | 3% |
| Naphthalene sulfonic acid formaldehyde condensate | 5% |
| Precipitated calcium carbonate | Make up to 100% |

Compound 2 and other components are fully mixed, after smashing through ultrafine pulverizer, 30% compound 2 wettable powders products were obtained.

Example 8

40% Suspension Concentrate

| Compound 367 | 40% |
| --- | --- |
| Glycol | 10% |
| Nonylphenols polyethylene glycol ether | 6% |
| Lignin sulfonate | 10% |
| Carboxymethyl cellulose | 1% |
| 37% formaldehyde aqueous solution | 0.2% |
| 75% of silicone oil water emulsion | 0.8% |
| Water | Make up to 100% |

Fully mixing compound 367 and other components, suspension concentrate can be obtained, and then any required concentration dilution can be obtained by diluting the above obtained concentrated suspension with water.

Example 9

60% Water Dispersible Granules

| Compound 367 | 60% |
| --- | --- |
| Naphthalene sulfonate formaldehyde condensate | 12% |
| N-methyl-N-oil acyl-bovine sodium | 8% |
| Polyvinylpyrrolidone | 2% |
| Carboxymethyl cellulose | 2% |
| Kaolin | Make up to 100% |

To mix compound 367 and other components, after smashing, kneading together with water, added to the granulation 10-100 mesh machine for granulation, then by drying and sieving (at the scope screen).

Test of Biological Activity

Example 10

Determination of Insecticidal and Acaricidal Activity

To determine the insecticidal and acaricidal activity of selected compounds by the following procedures:

Compounds were dissolved in mixed solvent (acetone:methanol=1:1), and diluted to required concentration with water containing 0.1% of tween 80.

The second instar larvae of diamond backmoth (*Plutella xylostella*) were used in biological test. The method of spraying by airbrush was employed.

Determination of insecticidal activity against diamond backmoth: The cabbage leaves were made into plates of 1 cm diameter by punch. A test solution (0.5 ml) was sprayed by airbrush at the pressure of 0.7 kg/cm$^2$ to both sides of every plate. 10 Second instar larvae were put into the petri-dishes after the leaf disc air-dried and 3 replicates were set for each treatment. Then the insects were maintained in observation room (25V, 60-70% R.H.). Scores were conducted and mortalities were calculated after 72 hrs.

Parts of test results are as follows:

At the dose of 100 mg/L, compound 1, 2, 8, 11, 13, 16, 17, 18, 24, 26, 38, 76, 77, 86, 92, 225, 247, 248, 257, 268, 269, 278, 280, 283, 284, 293, 306, 352, 356, 360, 361, 363, 367, 368, 377, 387, 389, 500, 522, 532, 538, 546 showed 100% control of the second instar larvae of diamond backmoth. At the same dose, contrast compound pyridalyl also showed 100% control.

At the dose of 25 mg/L, compound 2, 225, 247, 248, 268, 269, 352, 367, 377, 387 showed 100% control of the second instar larvae of diamond backmoth. At the same dose, contrast compound pyridalyl also showed 100% control.

At the dose of 6.25 mg/L, compound 2, 248, 367, 377, 387 showed above 80% control of the second instar larvae of diamond backmoth and compound 2, 367 showed more than 90% control. At the same dose, contrast compound pyridalyl also showed 65% control.

Example 11

Determination of Fungicidal Activity

Determination of fungicidal activities against plant diseases of selected compounds were carried out by the following procedure:

Determination of Fungicidal Activity In Vivo:

Plants were prepared in pot. Compounds were dissolved in acetone and diluted to required concentration by water containing 0.1% (wt) Tween80. Test solution was sprayed onto potted plant. Pathogen inoculation was carried out after 24 hours, then plants were hold in growth chambers maintaining constant temperature and moisture for infection. When untreated plant was under desirable disease severity (after 1 week approximately), assessment was carried out by visual observation.

Part of Test Results In Vivo:

At 400 ppm, compound 2 showed more than 70% control of wheat powdery mildew.

What is the claimed is:

1. Ether compounds with nitrogen-containing 5-member heterocycle represented by general formula (I):

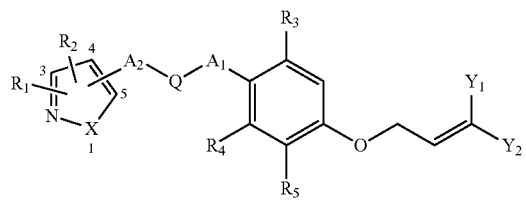

(I)

Wherein:

$R_1$ is selected from H, $CO_2R_6$, $C_1$-$C_6$alkyl, $C_1$-$C_6$haloalkyl, $C_1$-$C_6$alkoxy$C_1$-$C_6$alkyl, $C_1$-$C_6$haloalkoxy$C_1$-$C_6$alkyl, $C_3$-$C_6$cycloalkyl or $R_7$;

$R_2$ is selected from H, halo, CN, $CO_2R_6$, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$haloalkylthio, $C_3$-$C_6$cycloalkyl or $R_7$;

$R_3$ is Cl;

$R_4$ and $R_5$ mutually independently may be the same or different, selected from H or Cl;

X is selected from $NR_8$ or O;

$R_8$ is selected from $C_1$-$C_6$alkyl, $C_1$-$C_6$haloalkyl or $R_7$;

$Y_1$ and $Y_2$ are Cl;

$A_1$ and $A_2$ are O;

$R_6$ is selected from H or $C_1$-$C_6$alkyl;

$R_7$ is selected from phenyl, pyridinyl, furanyl, thiophen, thiazolyl or benzyl, or above group substituted with 1-3 substitutents selected from halo, $NO_2$, CN, $CO_2R_6$, $CONHR_6$, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfonyl, phenyl, 4-chloro-phenyl, phenoxy or 4-chloro-phenoxy;

Q is selected from —$CH_2CH_2$—, —$CH_2CH_2CH_2$— or —$CH_2CH_2CH_2CH_2$—;

$A_2$ links with heterocycle at the 3, 4 or 5-position; when $A_2$ links with heterocycle at the 5-position, $R_1$ is at 3-position, $R_2$ is at 4-position, the structure is represented by general formula I-1; when $A_2$ links with heterocycle at the 3-position, $R_1$ is at 5-position, $R_2$ is at 4-position, the structure is represented by general formula I-2; when $A_2$ links with heterocycle at the 4-position, $R_1$ is at 3-position, $R_2$ is at 5-position, the structure is represented by general formula I-3;

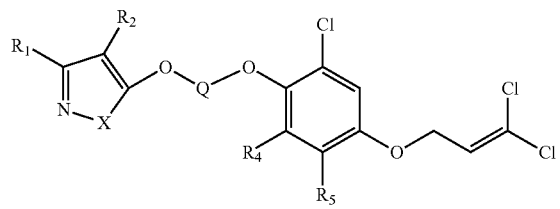

I-1

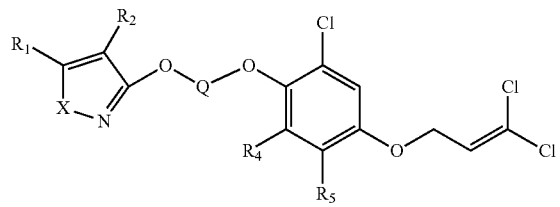

I-2

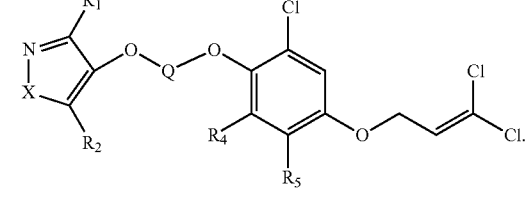

I-3

2. The compounds according to claim 1, wherein in general formula (I-1) or formula (I-2):

$R_1$ is selected from H, $CO_2R_6$, $C_1$-$C_6$alkyl, $C_1$-$C_6$haloalkyl, $C_1$-$C_6$alkoxy$C_1$-$C_6$alkyl, $C_1$-$C_6$haloalkoxy$C_1$-$C_6$alkyl, $C_3$-$C_6$cycloalkyl or $R_7$;

$R_2$ is selected from H, F, Cl, Br, CN, $CO_2R_6$ or $C_1$-$C_6$alkyl;

$R_4$ and $R_5$ mutually independently may be the same or different, selected from H or Cl;

X is $NR_8$;

$R_8$ is selected from $C_1$-$C_4$alkyl or $R_7$;

$R_6$ is selected from H or $C_1$-$C_4$alkyl;

$R_7$ is selected from phenyl, or phenyl substituted with 1-3 substitutents selected from F, Cl, Br, $C_1$-$C_6$alkyl, $C_1$-$C_6$haloalkyl, $C_1$-$C_6$alkoxy, $C_1$-$C_6$haloalkoxy or $C_1$-$C_6$alkylthio;

Q is selected from —CH$_2$CH$_2$—, —CH$_2$CH$_2$CH$_2$— or —CH$_2$CH$_2$CH$_2$CH$_2$—.

3. The compounds according to claim 1, wherein in general formula (I-3):
- R$_1$ is selected from H, CO$_2$R$_6$ or C$_1$-C$_6$alkyl;
- R$_2$ is selected from H, F, Cl, Br or C$_1$-C$_6$alkyl;
- R$_4$ and R$_5$ mutually independently may be the same or different, selected from H or Cl;
- X is NR$_8$;
- R$_8$ is selected from C$_1$-C$_4$alkyl or R$_7$;
- R$_6$ is selected from H or C$_1$-C$_4$alkyl;
- R$_7$ is selected from phenyl, or phenyl substituted with 1-3 substitutents selected from F, Cl, Br, CN, C$_1$-C$_6$haloalkyl, C$_1$-C$_6$alkoxy, C$_1$-C$_6$haloalkoxy or C$_1$-C$_6$alkylthio;
- Q is selected from —CH$_2$CH$_2$—, —CH$_2$CH$_2$CH$_2$— or —CH$_2$CH$_2$CH$_2$CH$_2$—.

4. The compounds according to claim 2, wherein in general formula (I-1) or formula (I-2):
- R$_1$ is selected from H, C$_1$-C$_6$alkyl, phenyl, or phenyl substituted with 1-3 substitutents selected from F, Cl, Br, C$_1$-C$_4$alkyl, C$_1$-C$_4$haloalkyl, C$_1$-C$_4$alkoxy, C$_1$-C$_4$haloalkoxy or C$_1$-C$_4$alkylthio;
- R$_2$ is selected from H, C$_1$ or C$_1$-C$_4$alkyl;
- R$_4$ and R$_5$ mutually independently may be the same or different, selected from H or Cl;
- X is NR$_8$;
- R$_8$ is selected from C$_1$-C$_4$alkyl, phenyl, or phenyl substituted with 1-3 substitutents selected from F, Cl, Br, C$_1$-C$_4$allyl, C$_1$-C$_4$haloalkyl, C$_1$-C$_4$alkoxy or C$_1$-C$_4$haloalkoxy;
- R$_6$ is selected from H or C$_1$-C$_4$alkyl;
- Q is selected from —CH$_2$CH$_2$—, —CH$_2$CH$_2$CH$_2$— or —CH$_2$CH$_2$CH$_2$CH$_2$—.

5. The compounds according to claim 3, wherein in general formula (I-3):
- R$_1$ is selected from H, CO$_2$R$_6$ or C$_1$-C$_4$alkyl;
- R$_2$ is selected from H, F, Cl, Br or C$_1$-C$_4$alkyl;
- R$_4$ and R$_5$ mutually independently may be the same or different, selected from H or Cl;
- X is NR$_8$;
- R$_8$ is selected from C$_1$-C$_4$alkyl, phenyl, or phenyl substituted with 1-3 substitutents selected from F, Cl, Br, C$_1$-C$_4$alkyl, C$_1$-C$_4$haloalkyl, C$_1$-C$_4$alkoxy or C$_1$-C$_4$haloalkoxy;
- R$_6$ is selected from H or C$_1$-C$_4$alkyl;
- Q is selected from —CH$_2$CH$_2$—, —CH$_2$CH$_2$CH$_2$— or —CH$_2$CH$_2$CH$_2$CH$_2$—.

6. A method of controlling insects which comprises applying a compound having general formula (I) according to claim 1 to agricultural and other fields.

7. A method of controlling fungi which comprises applying a compound having general formula (I) according to claim 1 to agricultural and other fields.

8. An insecticidal or fungicidal composition comprising a compound having general formula (I) of claim 1 as an active ingredient, wherein the weight percentage of the active ingredient in the composition is from 0.1-99%.

* * * * *